US011773438B2

(12) United States Patent
Wu et al.

(10) Patent No.: US 11,773,438 B2
(45) Date of Patent: *Oct. 3, 2023

(54) MODIFIED NUCLEOTIDE LINKERS

(71) Applicant: Illumina Cambridge Limited, Cambridge (GB)

(72) Inventors: Xiaolin Wu, Cambridge (GB); Xiaohai Liu, Cambridge (GB)

(73) Assignee: Illumina Cambridge Limited, Cambridge (GB)

(*) Notice: Subject to any disclaimer, the term of this patent is extended or adjusted under 35 U.S.C. 154(b) by 0 days.

This patent is subject to a terminal disclaimer.

(21) Appl. No.: 17/562,510

(22) Filed: Dec. 27, 2021

(65) Prior Publication Data

US 2022/0186306 A1 Jun. 16, 2022

Related U.S. Application Data

(60) Continuation of application No. 16/258,401, filed on Jan. 25, 2019, now Pat. No. 11,230,734, which is a division of application No. 14/821,251, filed on Aug. 7, 2015, now Pat. No. 10,190,157.

(30) Foreign Application Priority Data

Aug. 8, 2014 (GB) ...................... 1414098

(51) Int. Cl.
*C12Q 1/68* (2018.01)
*C07H 19/14* (2006.01)
*C12Q 1/6869* (2018.01)

(52) U.S. Cl.
CPC ........... *C12Q 1/6869* (2013.01); *C07H 19/14* (2013.01)

(58) Field of Classification Search
CPC .............................. C12Q 1/6869; C07H 19/04
See application file for complete search history.

(56) References Cited

U.S. PATENT DOCUMENTS

| | | |
|---|---|---|
| 6,379,698 B1 | 4/2002 | Leamon |
| 10,190,157 B2 | 1/2019 | Wu et al. |
| 11,230,734 B2 | 1/2022 | Wu et al. |
| 2007/0117104 A1 | 5/2007 | Buzby |
| 2007/0166705 A1 | 7/2007 | Milton et al. |
| 2009/0232833 A1 | 9/2009 | Zhao |
| 2010/0029494 A1 | 2/2010 | Cherkasov et al. |
| 2010/0093992 A1 | 4/2010 | Cherkasov et al. |
| 2010/0234444 A1 | 9/2010 | Zhao |
| 2011/0039259 A1 | 2/2011 | Ju |
| 2011/0039266 A1 | 2/2011 | Williams et al. |
| 2012/0156671 A1* | 6/2012 | Liu ...................... C12Q 1/6869 435/6.1 |
| 2012/0252691 A1 | 10/2012 | Etienne et al. |
| 2013/0079232 A1 | 3/2013 | Kain et al. |

FOREIGN PATENT DOCUMENTS

| | | |
|---|---|---|
| CN | 103087131 A | 5/2013 |
| CN | 103484106 A | 1/2014 |
| CN | 103866010 A | 6/2014 |
| JP | 2004-516810 | 6/2004 |
| WO | WO 00/036152 | 6/2000 |
| WO | WO 02/086088 | 10/2002 |
| WO | WO 02/088381 | 11/2002 |
| WO | WO 02/088382 | 11/2002 |
| WO | WO 03/048387 | 6/2003 |
| WO | WO 04/018493 | 3/2004 |
| WO | WO 04/090154 | 10/2004 |
| WO | WO 05/044836 | 5/2005 |
| WO | WO 07/020457 | 2/2007 |
| WO | WO 2007/135368 A2 | 11/2007 |
| WO | WO 08/034120 | 3/2008 |
| WO | WO 08/034122 | 3/2008 |
| WO | WO 08/034124 | 3/2008 |
| WO | WO 08/070749 | 6/2008 |
| WO | WO 08/144544 | 11/2008 |
| WO | WO 09/051807 | 4/2009 |
| WO | WO 09/054922 | 4/2009 |
| WO | WO 10/110775 | 9/2010 |
| WO | WO 12/159072 | 11/2012 |
| WO | WO 13/044018 | 3/2013 |
| WO | WO 13/074910 | 5/2013 |
| WO | WO 14/135221 | 9/2014 |
| WO | WO 14/135223 | 9/2014 |
| WO | WO 15/170102 | 11/2015 |

OTHER PUBLICATIONS

Guo J. et al., Four-color DNA sequencing with 3′-O-modified nucleotide reversible terminators and chemically cleavable fluorescent dideoxynucleotides. PNAS, Jul. 8, 2008, vol. 105, No. 27, pp. 9145-9150.

Jayasekara et al., 4-Alkyloxyimino Derivatives of Uridine-5′-triphosphate: Distal Modification of Potent Agonists as a Strategy for Molecular Probes of P2Y2, P2Y4, and P2Y6 Receptors, J Med Chem. 2014; 57(9): 3874-3883.

Nampalli et al., "Fluorescence resonance energy transfer terminators for DNA sequencing", Tetrahedron Letters 41 (2000) 8867-8871.

Turcatti et al. 2008. A new class of cleavable fluorescent nucleotides: Synthesis and optimization as reversible terminators for DNA sequencing by synthesis. Nuc. Acid. Res., 36(4):e25/1-e25/13.

International Search Report and Written Opinion for Application No. PCT/GB2015/052282, dated Dec. 1, 2015.

* cited by examiner

*Primary Examiner* — Jezia Riley

(74) *Attorney, Agent, or Firm* — Knobbe, Martens, Olson & Bear, LLP

(57) ABSTRACT

Some embodiments of the present application relate to novel modified nucleotide linkers for increasing the efficiency of nucleotide incorporation in Sequencing by Synthesis applications. Methods of preparing these modified nucleotide linkers are also provided herewith.

27 Claims, 17 Drawing Sheets

| Dye set | Density | %PF | Ph R1 | PPh R1 | Ph R2 | PPh R2 | %Align R1 | %Align R2 | error R1 | error R2 |
|---|---|---|---|---|---|---|---|---|---|---|
| V4 | 230 | 79.6 | 0.205 | 0.111 | 0.35 | 0.149 | 82.2 | 79.3 | 1.41 | 3.19 |
| V5.75 | 187 | 77.65 | 0.371 | 0.048 | 0.442 | 0.164 | 80.06 | 79.99 | 2.16 | 3.94 |
| V10/cyan-peg4 | 222 | 79.88 | 0.305 | 0.084 | 0.53 | 0.179 | 81.89 | 79.45 | 1.42 | 3.48 |
| V10/cyan-peg4, A-AEDI550S0 | 223 | 81.83 | 0.14 | 0.123 | 0.294 | 0.197 | 81.61 | 67.12 | 0.85 | 5.84 |
| V10/cyan-peg4, A-AcLys550S0 | 227 | 78.52 | 0.2 | 0.128 | 0.319 | 0.272 | 82.23 | 78.52 | 1.44 | 3.48 |
| V10/cyan, A-AcLys550S0 | 145 | 86.27 | 0.178 | 0.211 | 0.283 | 0.29 | 82.4 | 79.84 | 1.33 | 3.33 |

FIG. 4

| Dye set | Density | %PF | Ph R1 | PPh R1 | Ph R2 | PPh R2 | %Align R1 | %Align R2 | error R1 | error R2 |
|---|---|---|---|---|---|---|---|---|---|---|
| V4 | 191 | 82.62 | 0.132 | 0.151 | 0.242 | 0.163 | 81.91 | 79.59 | 1.34 | 2.43 |
| V5.75 | 235 | 79.02 | 0.212 | 0.05 | 0.304 | 0.187 | 82.54 | 78.74 | 1.4 | 4.2 |
| V10/Cyan-peg4 | 213 | 84.7 | 0.2 | 0.063 | 0.348 | 0.179 | 83.3 | 81.19 | 0.96 | 2.02 |
| V10/Cyan-peg4 | 220 | 83.03 | 0.188 | 0.115 | 0.317 | 0.207 | 82.92 | 80.9 | 1.11 | 2.16 |
| V10/Cyan-peg4,A-AEDI-550SO | 252 | 76.37 | 0.102 | 0.097 | 0.132 | 0.412 | 80.1 | 34.9 | 0.84 | 25.58 |
| V10/Cyan-peg4,A-ACA550SO | 204 | 85.88 | 0.145 | 0.076 | 0.271 | 0.222 | 83.21 | 80.58 | 0.96 | 2.39 |

FIG. 6

| ffA | K (uM/min) |
|---|---|
| NR550S0 | 22 (1X) |
| -SS-NR550S0 | 54 (2X) |
| -AEDI-NR550S0 | 97 (4X) |
| Std -SO7181 | 99 (4X) |

V10 combination with different A-550S0
(same concentration) Scatter plot for tile 1 cycle 2

| Dye set | Density | %PF | Ph R1 | PPh R1 | Ph R2 | PPh R2 | %Align R1 | %Align R2 | error R1 | error R2 |
|---|---|---|---|---|---|---|---|---|---|---|
| ffNs + ffA-NR550S0 | 222 | 79.88 | 0.305 | 0.084 | 0.53 | 0.179 | 81.89 | 79.45 | 1.42 | 3.48 |
| ffNs + ffA-AEDI-NR550S0 | 223 | 81.83 | 0.14 | 0.123 | 0.294 | 0.197 | 81.61 | 67.12 | 0.88 | 5.84 |
| ffNs + ffA-AcLys-NR550S0 | 227 | 78.52 | 0.2 | 0.128 | 0.319 | 0.272 | 82.23 | 78.52 | 1.44 | 3.48 |
| ffNs + ffA-BocLys-NR550S0 | 211 | 82.97 | 0.126 | 0.146 | 0.226 | 0.249 | 82.54 | 80.45 | 1.17 | 1.99 |

FIG. 12A

MODIFIED NUCLEOTIDE LINKERS

INCORPORATION BY REFERENCE TO ANY PRIORITY APPLICATIONS

The present application is a continuation of U.S. application Ser. No. 16/258,401, filed Jan. 25, 2019, which is a division of U.S. application Ser. No. 14/821,251, filed Aug. 7, 2015, now U.S. Pat. No. 10,190,157, which claims the benefit of priority to Great Britain Application No. 1414098.2, filed Aug. 8, 2014, each of which are hereby incorporated by reference in its entirety.

FIELD

Some embodiments of the present application relate to novel nucleoside or nucleotide linkers for increasing incorporation of nucleotides in DNA sequencing and other diagnostic applications, for example, sequencing by synthesis.

BACKGROUND

Advances in the study of molecules have been led, in part, by improvement in technologies used to characterize the molecules or their biological reactions. In particular, the study of the nucleic acids DNA and RNA has benefited from developing technologies used for sequence analysis and the study of hybridization events.

An example of the technologies that have improved the study of nucleic acids is the development of fabricated arrays of immobilized nucleic acids. These arrays typically have a high-density matrix of polynucleotides immobilized onto a solid support material. See, e.g., Fodor et al., *Trends Biotech.* 12: 19-26, 1994, which describes ways of assembling different nucleic acids using a chemically sensitized glass surface protected by a mask, but exposed at defined areas to allow attachment of suitably modified nucleotide phosphoramidites. Fabricated arrays can also be manufactured by the technique of "spotting" known polynucleotides onto a solid support at predetermined positions (e.g., Stimpson et al., *Proc. Natl. Acad. Sci.* 92: 6379-6383, 1995).

One way of determining the nucleotide sequence of a nucleic acid bound to an array is called "sequencing by synthesis" or "SBS". This technique for determining the nucleotide sequence of DNA ideally requires the controlled (i.e., one at a time) incorporation of the correct complementary nucleotide opposite the nucleic acid being sequenced. This allows for accurate sequencing by adding nucleotides in multiple cycles as each nucleotide residue is sequenced one at a time, thus preventing the incorporation of an uncontrolled series of nucleotides. Each incorporated nucleotide is read using an appropriate label attached thereto before removal of the label moiety and the subsequent next round of sequencing.

Accordingly, in the context of nucleic acid sequencing reactions it would be desirable to be able to increase the rate of nucleotide incorporation during sequencing by synthesis so that the efficiency of the sequencing method can be improved.

SUMMARY

Some embodiments disclosed herein relate to a nucleoside or nucleotide covalently attached to a fluorophore through a linker, wherein said linker comprises a structure of formula (I) or (II), or a combination of both:

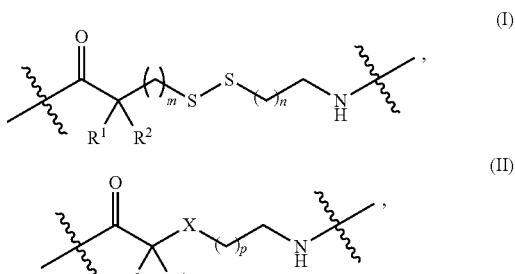

each $R^1$ and $R^2$ is independently selected from hydrogen or optionally substituted $C_{1-6}$ alkyl;

$R^3$ is selected from hydrogen, optionally substituted $C_{1-6}$ alkyl, $-NR^5-C(=O)R^6$, or $-NR^7-C(=O)-OR^8$;

$R^4$ is selected from hydrogen or optionally substituted $C_{1-6}$ alkyl;

each $R^5$ and $R^7$ is independently selected from hydrogen, optionally substituted $C_{1-6}$ alkyl, optionally substituted phenyl, or optionally substituted $C_{7-12}$ aralkyl;

each $R^6$ and $R^8$ is independently selected from optionally substituted $C_{1-6}$ alkyl, optionally substituted phenyl, optionally substituted $C_{7-12}$ aralkyl, optionally substituted $C_{3-7}$ cycloalkyl, or optionally substituted 5 to 10 membered heteroaryl;

each of the methylene repeating unit in

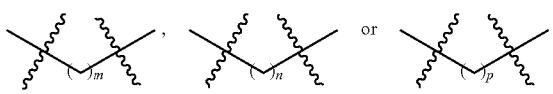

is optionally substituted;

X is selected from methylene ($CH_2$), oxygen (O), or sulfur (S);

m is an integer of 0 through 20;

n is an integer of 1 through 20; and p is an integer of 1 through 20.

In some embodiments, the fluorophore labeled nucleoside or nucleotide comprises a structure of formula (I) does not have the structure:

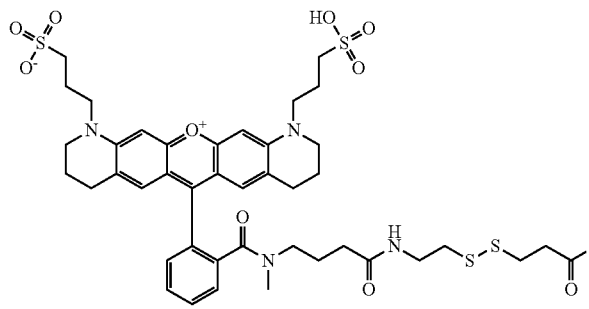
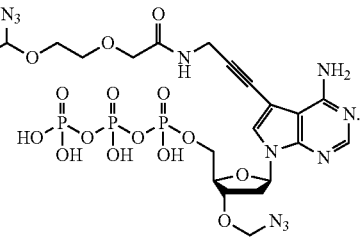

Some embodiments disclosed herein relate to a nucleoside or nucleotide covalently attached to a fluorophore through a linker, wherein said linker comprises a structure of formula (III):

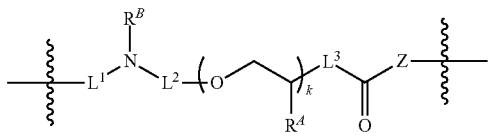

wherein $L^1$ is absent or comprises a linker of any one described in formula (I) or (II), or a protecting moiety, or combinations thereof; $L^2$ is selected from optionally substituted $C_{1-20}$ alkylene, optionally substituted $C_{1-20}$ heteroalkylene, optionally substituted $C_{1-20}$ alkylene interrupted by a substituted aromatic group, or optionally substituted $C_{1-20}$ heteroalkylene interrupted by a substituted aromatic group; $L^3$ is selected from optionally substituted $C_{1-20}$ alkylene, or optionally substituted $C_{1-20}$ heteroalkylene; $R^A$ is selected from hydrogen, cyano, hydroxy, halogen, $C_{1-6}$ alkyl, $C_{1-6}$ alkoxy, $C_{1-6}$ haloalkyl, $C_{1-6}$ haloalkoxy, or azido, and wherein at least one of the repeating units of

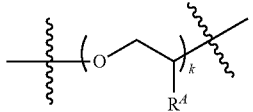

comprises an azido group; Z is selected from oxygen (O) or $NR^B$; each $R^B$ and $R^C$ is independently selected from hydrogen or optionally substituted $C_{1-6}$ alkyl; and k is an integer of 1 through 50.

Some embodiments disclosed herein relate to kits comprising a labeled nucleoside or nucleotide comprising a linker between the fluorophore and the nucleoside or nucleotide, wherein the linker comprises a structure of any one of formula (I), (II) or (III), or combinations thereof.

Some embodiments disclosed herein relate to reagents for modifying a nucleoside or a nucleotide comprising a fluorophore and a linker, wherein the linker comprises a structure of any one of formula (I), (II) or (III), or combinations thereof.

Some embodiments disclosed herein relate to methods for detecting a nucleoside that has been incorporated into a polynucleotide, comprising: (a) incorporating a labeled nucleoside or nucleotide comprising a linker into a polynucleotide; and (b) detecting a fluorescent signal from said labeled nucleoside or nucleotide that was incorporated in step (a), wherein the linker comprises a structure of any one of formula (I), (II) or (III), or combinations thereof. In some embodiments, the method further comprises: providing a template nucleic acid strand and a partially hybridized nucleic acid strand, wherein step (a) incorporates into the hybridized strand at least one nucleoside or nucleotide that is complementary to a nucleoside or nucleotide at the corresponding position of the template strand, and wherein step (b) identifies the base of the incorporated nucleoside or nucleotide, thereby indicating the identity of the complementary nucleoside or nucleotide of the template strand.

Some embodiments disclosed herein relate to methods of sequencing a template nucleic acid molecule, comprising: incorporating one or more labeled nucleotides into a strand of nucleic acid complementary to the template nucleic acid; determining the identity of the base present in one or more incorporated labeled nucleotides in order to determine the sequence of the template nucleic acid molecule; wherein the identity of the base present in the one or more labeled nucleotides is determined by detecting a fluorescent signal produced by said labeled nucleotides; and wherein at least one incorporated labeled nucleotide comprising a linker as described above, wherein the linker comprises a structure of any one of formula (I), (II) or (III), or combinations thereof. In some embodiments, the identity of the base present in the one or more nucleotides is determined after each nucleotide incorporation step.

BRIEF DESCRIPTION OF THE DRAWINGS

FIG. 4 shows a data table of a two dye sequencing run used to evaluate the effect of 125 insert of FIG. 1B and the 315 insert of FIG. 3B on sequencing quality.

FIG. 6 shows a data table a sequencing run used to evaluate the effect of the 125 insert of FIG. 1B and the 310 insert of FIG. 3A on sequencing quality.

FIG. 10A is a graph showing the rate of incorporation at 1 uM with FIG. 10B showing the tabulated results. FIG. 10C diagrammatically shows the AEDI and SS linkers with NR550S0.

FIGS. 12A and 12B show sequencing metrics on M111, Human550, 2×151 cycles.

DETAILED DESCRIPTION OF THE PREFERRED EMBODIMENTS

Figure 1A:
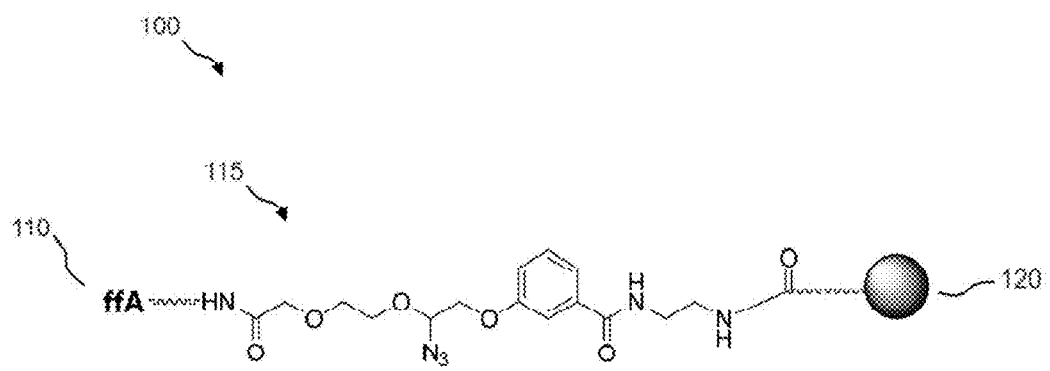
FIG. 1A illustrates a partial linking group structural of a standard labeled nucleotide.

Some embodiments disclosed herein relate to a nucleoside or nucleotide covalently attached to a fluorophore through a linker, wherein the linker comprises a structure of formula (I) or (II) below, or combination of both, wherein the definitions of the variables are defined above.

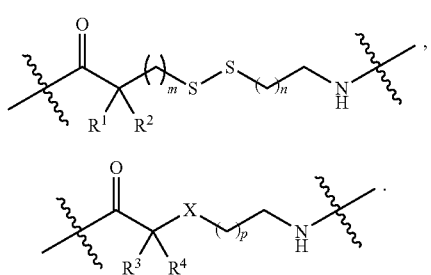

In some embodiments of the structure of formula (I), $R^1$ is hydrogen. In some other embodiments, $R^1$ is optionally substituted $C_{1-6}$ alkyl. In some such embodiments, $R^1$ is methyl.

In any embodiments of $R^1$ as described herein of formula (I), $R^2$ is hydrogen. In some other embodiments, $R^2$ is optionally substituted $C_{1-6}$ alkyl. In some such embodiments, $R^2$ is methyl. In one embodiment, both $R^1$ and $R^2$ are methyl. In another embodiment, both $R^1$ and $R^2$ are hydrogen.

In some embodiments of the structure of formula (I), m is 0. In some other embodiments, m is 1.

In some embodiments of the structure of formula (I), n is 1.

In some embodiments of the structure of formula (I), the structure of formula (I) can also be represented by formula (Ia) or (Ib):

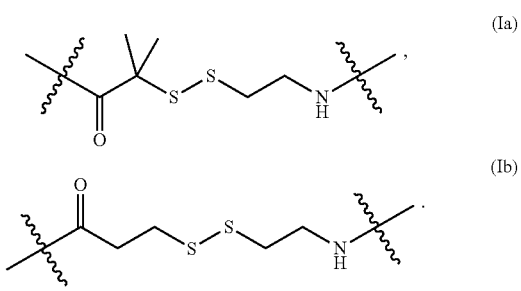

In some embodiments described herein, formula (Ia) is referred to as "AEDI" and formula (Ib) is referred to as "SS."

In some embodiments of the structure of formula (II), $R^3$ is hydrogen. In some other embodiments, $R^3$ is optionally substituted $C_{1-6}$ alkyl. In some such embodiments, $R^3$ is methyl. In some embodiments, $R^3$ is —$NR^5$—$C(=O)R^6$. In some such embodiments, $R^5$ is hydrogen. In some such embodiments, $R^6$ is optionally substituted $C_{1-6}$ alkyl, for example, methyl. In some embodiments, $R^3$ is —$NR^7$—C(=O)O$R^8$. In some such embodiments, $R^7$ is hydrogen. In some such embodiments, $R^8$ is optionally substituted $C_{1-6}$ alkyl, for example, t-butyl.

In any embodiments of $R^3$ as described herein of formula (II), $R^4$ is hydrogen. In some other embodiments, $R^4$ is optionally substituted $C_{1-6}$ alkyl. In some such embodiments, $R^4$ is methyl. In one embodiment, both $R^3$ and $R^4$ are methyl. In another embodiment, both $R^3$ and $R^4$ are hydrogen. In one embodiment, $R^3$ is —NH(C=O)$CH_3$ and $R^4$ is hydrogen. In another embodiment, $R^3$ is —NH(C=O)O$^t$Bu (Boc) and $R^4$ is hydrogen.

In some embodiments of the structure of formula (II), X is methylene, which can be optionally substituted. In another embodiment, X is oxygen (O). In yet another embodiment, X is sulfur (S).

In some embodiments of the structure of formula (II), p is 1. In some other embodiments, p is 2.

In some embodiments of the structure of formula (II), the structure of formula (II) can also be represented by formula (IIa), (IIb), (IIc), (IId), (IIe) or (IIf):

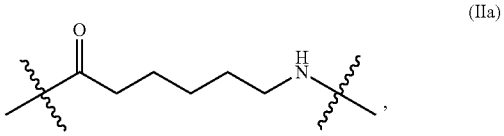

-continued

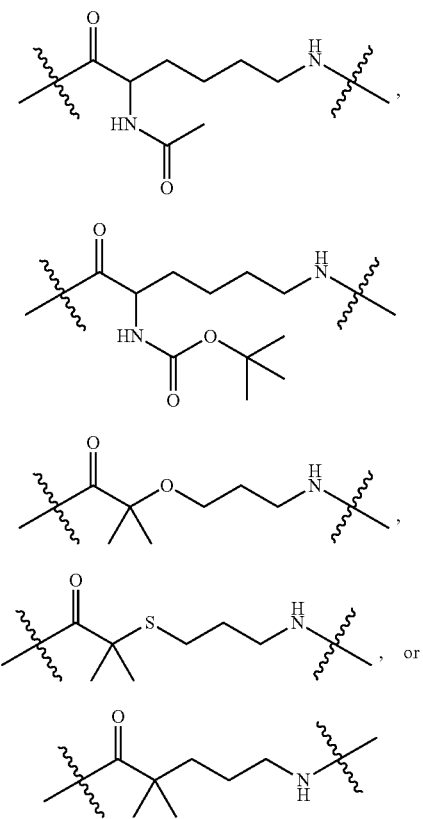

In some embodiments described herein, formula (IIa) is referred to as "ACA," formula (IIb) is referred to as "AcLys," formula (IIc) is referred to as "BocLys," formula (IId) is referred to as "dMeO," formula (IIe) is referred to as "dMeS," and formula (IIf) is referred to as "DMP."

In any embodiments of the fluorophore labeled nucleoside or nucleotide through a linker comprising a structure of formula (I) or (II) as described herein, the nucleoside or nucleotide can be attached to the left side of the linker, either directly, or through additional linking moiety.

Some embodiments disclosed herein relate to a nucleoside or nucleotide covalently attached to a fluorophore through a linker, said linker comprising a structure of formula (III), and wherein the definitions of the variables are defined above.

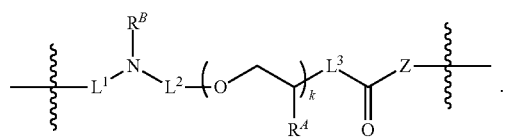

In some embodiments of the structure of formula (III), $L^1$ is absent. In some other embodiments, $L^1$ is a linker described above comprising the structure of formula (I) or (II), in particular formula (Ia), (Ib), (II), (IIa), (IIb), (IIc), (IId), (IIe) or (IIf). In some other embodiments, $L^1$ can be a protecting moiety comprising molecule that protects against DNA damage. In some such embodiments, protecting moiety comprises Trolox, gallic acid, p-nitro-benzyl (pNB), or ascorbate, or combinations thereof.

In some embodiments of the structure of formula (III), $L^2$ is optionally substituted $C_{1-20}$ alkylene. In some further embodiments, $L^2$ is optionally substituted $C_{4-10}$ alkylene. In some such embodiments, $L^2$ is heptylene. In some other embodiments, $L^2$ is optionally substituted $C_{1-20}$ heteroalkylene. In some such embodiments, the optionally substituted $C_{1-20}$ heteroalkylene comprises one or more nitrogen atoms. In some such embodiments, at least one of the carbon atom of the $C_{1-20}$ heteroalkylene is substituted with oxo (=O). In some further embodiments, $L^2$ is optionally substituted $C_{3-6}$ heteroalkylene. In some embodiments, $L^2$ is interrupted by a substituted aromatic group, such as a substituted $C_{6-10}$ aryl group, or 5 to 10 membered substituted heteroaryl groups comprising one to three heteroatoms. In some such embodiments, $L^2$ is interrupted by a substituted phenyl group. In some such embodiments, the phenyl group is substituted with one or more (up to four) substituents selected from nitro, cyano, halo, hydroxy, $C_{1-6}$ alkyl, $C_{1-6}$ alkoxy, $C_{1-6}$ haloalkyl, $C_{1-6}$ haloalkoxy or sulfonyl hydroxide. In some further such embodiments, the phenyl group is substituted with one to four substituents selected from nitro, cyano, halo, or sulfonyl hydroxide (i.e., —S(=O)$_2$OH).

In some embodiments of the structure of formula (III), $R^A$ in

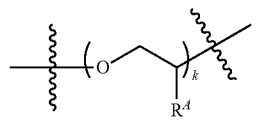

is selected from hydrogen or azido. In some such embodiments, k is 2 with one $R^A$ being azido and the other being hydrogen.

In some embodiments of the structure of formula (III), $L^3$ is optionally substituted $C_{1-20}$ alkylene. In some further embodiments, $L^3$ is optionally substituted $C_{1-6}$ alkylene. In some such embodiments, $L^3$ is ethylene. In some other embodiments, $L^3$ is optionally substituted $C_{1-20}$ heteroalkylene. In some such embodiments, the optionally substituted $C_{1-20}$ heteroalkylene comprises one or more oxygen atoms. In some such embodiments, $L^1$ is optionally substituted $C_{1-6}$ alkylene oxide, for example, $C_{1-3}$ alkylene oxide.

In some embodiments of the structure of formula (III), $R^B$ is hydrogen. In some embodiments, $R^c$ is hydrogen. In some further embodiments, both $R^B$ and $R^c$ are hydrogen.

In some embodiments of the structure of formula (III), the structure of formula (III) can also be represented by formula (IIIa), (IIIb) or (IIIc):

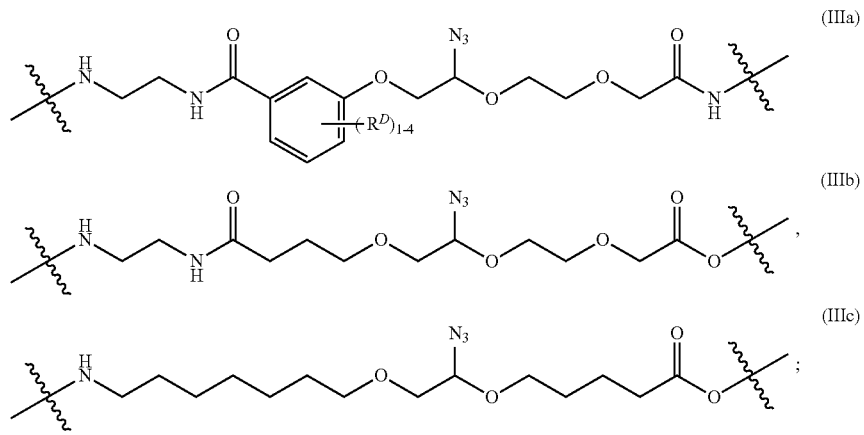

wherein $R^D$ is selected from nitro, cyano, halo, hydroxy, $C_{1-6}$ alkyl, $C_{1-6}$ alkoxy, $C_{1-6}$ haloalkyl, $C_{1-6}$ haloalkoxy or sulfonyl hydroxide. In some further embodiments, $R^D$ is selected from nitro, cyano, halo, or sulfonyl hydroxide.

In any embodiments of the fluorophore labeled nucleoside or nucleotide through a linker comprising a structure of formula (III) as described herein, the fluorophore can be attached to the left side of the linker, either directly, or through additional linking moiety.

In any embodiments described herein with respect to a linker comprising a structure of formula (I), (II) or (III), when the term "optionally substituted" is used to define a variable, such variable can be unsubstituted.

Definitions

Unless defined otherwise, all technical and scientific terms used herein have the same meaning as is commonly understood by one of ordinary skill in the art. The use of the term "including" as well as other forms, such as "include", "includes," and "included," is not limiting. The use of the term "having" as well as other forms, such as "have", "has," and "had," is not limiting. As used in this specification, whether in a transitional phrase or in the body of the claim, the terms "comprise(s)" and "comprising" are to be interpreted as having an open-ended meaning. That is, the above terms are to be interpreted synonymously with the phrases "having at least" or "including at least." For example, when used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

The section headings used herein are for organizational purposes only and are not to be construed as limiting the subject matter described.

As used herein, common organic abbreviations are defined as follows:

Ac Acetyl
Ac₂O Acetic anhydride
aq. Aqueous
Bn Benzyl
Bz Benzoyl
BOC or Boc tert-Butoxycarbonyl
Bu n-Butyl
cat. Catalytic
° C. Temperature in degrees Centigrade
CHAPS 3-[(3-Cholamidopropyl)dimethylammonio]-1-propanesulfonate
dATP Deoxyadenosine triphosphate
dCTP Deoxycytidine triphosphate
dGTP Deoxyguanosine triphosphate
dTTP Deoxythymidine triphosphate
ddNTP(s) Dideoxynucleotide(s)
DCM Methylene chloride
DMA Dimethylacetamide
DMAP 4-Dimethylaminopyridine
DMF N,N'-Dimethylformamide
DMSO Dimethylsulfoxide
DSC N,N'-Disuccinimidyl carbonate
EDTA Ethylene diamine tetra-acetic acid
Et Ethyl
EtOAc Ethyl acetate
ffN Fully functional nucleotide
ffA Fully functionalized adenosine nucleotide
g Gram(s)
GPC Gel permeation chromatography
h or hr Hour(s)
Hunig's base N,N-Diisopropylethylamine
iPr Isopropyl
KPi 10 mM potassium phosphate buffer at pH 7.0
IPA Isopropyl Alcohol
LCMS Liquid chromatography-mass spectrometry
LDA Lithium diisopropylamide
m or min Minute(s)
MeCN Acetonitrile
mL Milliliter(s)
PEG Polyethylene Glycol
PG Protecting group
Ph Phenyl
pNB p-nitro-benzyl
ppt Precipitate
rt Room temperature
SBS Sequencing by Synthesis
—S(O)₂OH Sulfonyl Hydroxide
TEA Triethylamine
TEAB Tetraethylammonium bromide
TFA Trifluoracetic acid
Tert, t tertiary
THF Tetrahydrofuran
TLC Thin Layer Chromatography TSTU O—(N-Succinimidyl)-N,N,N',N'-tetramethyluronium tetrafluoroborate μL Microliter(s)

As used herein, the term "array" refers to a population of different probe molecules that are attached to one or more substrates such that the different probe molecules can be differentiated from each other according to relative location. An array can include different probe molecules that are each located at a different addressable location on a substrate. Alternatively or additionally, an array can include separate substrates each bearing a different probe molecule, wherein the different probe molecules can be identified according to the locations of the substrates on a surface to which the substrates are attached or according to the locations of the substrates in a liquid. Exemplary arrays in which separate substrates are located on a surface include, without limitation, those including beads in wells as described, for example, in U.S. Pat. No. 6,355,431 B 1, US 2002/0102578 and PCT Publication No. WO 00/63437. Exemplary formats that can be used in the invention to distinguish beads in a liquid array, for example, using a microfluidic device, such as a fluorescent activated cell sorter (FACS), are described, for example, in U.S. Pat. No. 6,524,793. Further examples of arrays that can be used in the invention include, without limitation, those described in U.S. Pat. Nos. 5,429,807; 5,436,327; 5,561,071; 5,583,211; 5,658,734; 5,837,858; 5,874,219; 5,919,523; 6,136,269; 6,287,768; 6,287,776; 6,288,220; 6,297,006; 6,291,193; 6,346,413; 6,416,949; 6,482,591; 6,514,751 and 6,610,482; and WO 93/17126; WO 95/11995; WO 95/35505; EP 742 287; and EP 799 897.

As used herein, the term "covalently attached" or "covalently bonded" refers to the forming of a chemical bonding that is characterized by the sharing of pairs of electrons between atoms. For example, a covalently attached polymer coating refers to a polymer coating that forms chemical bonds with a functionalized surface of a substrate, as compared to attachment to the surface via other means, for example, adhesion or electrostatic interaction. It will be appreciated that polymers that are attached covalently to a surface can also be bonded via means in addition to covalent attachment.

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3-$, $CH_3CH_2-$, $CH_3CH_2CH_2-$, $(CH_3)_2CH-$, $CH_3CH_2CH_2CH_2-$, $CH_3CH_2CH(CH_3)-$ and $(CH_3)_3C-$.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like. The alkyl group may be substituted or unsubstituted.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "heteroalkyl" refers to a straight or branched hydrocarbon chain containing one or more heteroatoms, that is, an element other than carbon, including but not limited to, nitrogen, oxygen and sulfur, in the chain backbone. The heteroalkyl group may have 1 to 20 carbon atom, although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 4 carbon atoms. The heteroalkyl group may be designated as "$C_{1-4}$ heteroalkyl" or similar designations. The heteroalkyl group may contain one or more heteroatoms. By way of example only, "$C_{1-4}$ heteroalkyl" indicates that there are one to four carbon atoms in the heteroalkyl chain and additionally one or more heteroatoms in the backbone of the chain.

As used herein, "alkylene" means a branched, or straight chain fully saturated di-radical chemical group containing only carbon and hydrogen that is attached to the rest of the molecule via two points of attachment (i.e., an alkanediyl). The alkylene group may have 1 to 20 carbon atoms, although the present definition also covers the occurrence of the term alkylene where no numerical range is designated. The alkylene group may also be a medium size alkylene having 1 to 9 carbon atoms. The alkylene group could also be a lower alkylene having 1 to 4 carbon atoms. The alkylene group may be designated as "$C_{1-4}$alkylene" or similar designations. By way of example only, "$C_{1-4}$ alkylene" indicates that there are one to four carbon atoms in the alkylene chain, i.e., the alkylene chain is selected from the group consisting of methylene, ethylene, ethan-1,1-diyl, propylene, propan-1,1-diyl, propan-2,2-diyl, 1-methyl-ethylene, butylene, butan-1,1-diyl, butan-2,2-diyl, 2-methyl-propan-1,1-diyl, 1-methyl-propylene, 2-methyl-propylene, 1,1-dimethyl-ethylene, 1,2-dimethyl-ethylene, and 1-ethyl-ethylene. As used herein, when an alkylene is interrupted by an aromatic group, it refers to the insertion of an aromatic group between one carbon-carbon bond of the alkylene chain via two point of attachment or the attachment of an aromatic group to one terminal of the alkylene chain via one point of attachment. For example, when a n-butylene is interrupted by a phenyl group, exemplary structures include

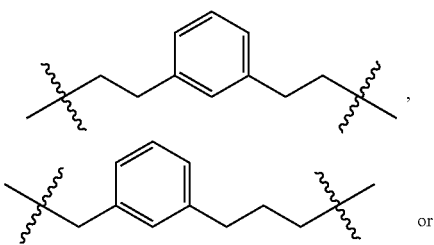

or

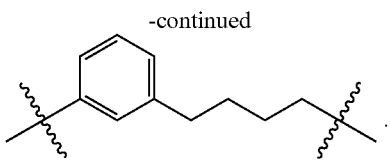

As used herein, the term "heteroalkylene" refers to an alkylene chain in which one or more skeletal atoms of the alkylene are selected from an atom other than carbon, e.g., oxygen, nitrogen, sulfur, phosphorus or combinations thereof. The heteroalkylene chain can have a length of 2 to 20,000. Exemplary heteroalkylenes include, but are not limited to, —OCH$_2$—, —OCH(CH$_3$)—, —OC(CH$_3$)$_2$—, —OCH$_2$CH$_2$—, —CH(CH$_3$)O—, —CH$_2$OCH$_2$—, —CH$_2$OCH$_2$CH$_2$—, —SCH$_2$—, —SCH(CH$_3$)—, —SC(CH$_3$)$_2$—, —SCH$_2$CH$_2$—, —CH$_2$SCH$_2$CH$_2$—, —NHCH$_2$—, —NHCH(CH$_3$)—, —NHC(CH$_3$)$_2$—, —NHCH$_2$CH$_2$—, —CH$_2$NHCH$_2$—, —CH$_2$NHCH$_2$CH$_2$—, and the like. As used herein, when a heteroalkylene is interrupted by an aromatic group, it refers to the insertion of an aromatic group between one carbon-carbon bond or carbon-heteroatom bond of the heteroalkylene chain via two point of attachment or the attachment of an aromatic group to one terminal of the heteroalkylene chain via one point of attachment. For example, when a n-propylene oxide is interrupted by a phenyl group, exemplary structures include

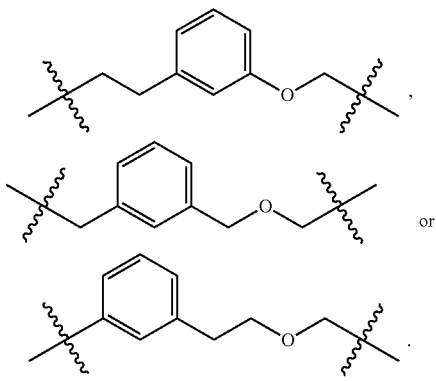

As used herein, "alkenyl" refers to an alkyl group that contains in the straight or branched hydrocarbon chain one or more double bonds. An alkenyl group may be unsubstituted or substituted.

As used herein, "alkynyl" refers to an alkyl group that contains in the straight or branched hydrocarbon chain one or more triple bonds. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s). In some embodiments, cycloalkyl groups can contain 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl, and cyclooctyl.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "C$_{6-10}$ aryl," "C$_6$ or C$_{10}$ aryl," or similar designations. Examples of aryl groups include, but are not limited to, phenyl, naphthyl, azulenyl, and anthracenyl.

An "aralkyl" or "arylalkyl" is an aryl group connected, as a substituent, via an alkylene group, such as "C$_{7-14}$ aralkyl" and the like, including but not limited to benzyl, 2-phenylethyl, 3-phenylpropyl, and naphthylalkyl. In some cases, the alkylene group is a lower alkylene group (i.e., a C$_{1-4}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a C$_{1-4}$ alkylene group).

As used herein, "cycloalkyl" means a fully saturated carbocyclyl ring or ring system. Examples include cyclopropyl, cyclobutyl, cyclopentyl, and cyclohexyl.

An "O-carboxy" group refers to a "—OC(=O)R" group in which R is selected from hydrogen, C$_{1-6}$ alkyl, C$_{2-6}$ alkenyl, C$_{2-6}$ alkynyl, C$_{3-7}$ carbocyclyl, C$_{6-10}$ aryl, 5-10 membered heteroaryl, and 5-10 membered heterocyclyl, as defined herein.

A "C-carboxy" group refers to a "—C(=O)OR" group in which R is selected from hydrogen, C$_{1-6}$ alkyl, C$_{2-6}$ alkenyl, C$_{2-6}$ alkynyl, C$_{3-7}$ carbocyclyl, C$_{6-10}$ aryl, 5-10 membered heteroaryl, and 5-10 membered heterocyclyl, as defined herein. A non-limiting example includes carboxyl (i.e., —C(=O)OH).

A "cyano" group refers to a "—CN" group.

A "azido" group refers to a "—N$_3$" group.

An "O-carbamyl" group refers to a "—OC(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-carbamyl" group refers to an "—N($R_A$)OC(=O)$R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-amido" group refers to a "—C(=O)$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-amido" group refers to a "—N($R_A$)C(=O)$R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "amino" group refers to a "—$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. A non-limiting example includes free amino (i.e., —NH2).

As used herein, the term "Trolox" refers to 6-hydroxy-2,5,7,8-tetramethylchroman-2-carboxylic acid.

As used herein, the term "ascorbate" refers to the salt of ascorbic acid.

As used herein, the term "gallic acid" refers to 3,4,5-trihydroxybenzoic acid.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_{1-6}$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., —$CF_3$), halo($C_1$-$C_6$)alkoxy (e.g., —$OCF_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —$CH_2$—, —$CH_2CH_2$—, —$CH_2CH(CH_3)CH_2$—, and the like. Similarly, a group identified as amino that requires two points of attachment includes di-radicals such as —NH—, —N($CH_3$)—, and the like. Other radical naming conventions clearly indicate that the radical is a di-radical such as "alkylene" or "alkenylene."

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

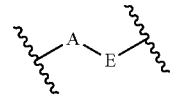

includes the substituent being oriented such that the A is attached at the leftmost attachment point of the molecule as well as the case in which A is attached at the rightmost attachment point of the molecule.

Where the compounds disclosed herein have at least one stereocenter, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein.

As used herein, a "nucleotide" includes a nitrogen containing heterocyclic base, a sugar, and one or more phosphate groups. They are monomeric units of a nucleic acid sequence. In RNA, the sugar is a ribose, and in DNA a deoxyribose, i.e. a sugar lacking a hydroxyl group that is present in ribose. The nitrogen containing heterocyclic base can be purine or pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine.

As used herein, a "nucleoside" is structurally similar to a nucleotide, but is missing the phosphate moieties. An example of a nucleoside analogue would be one in which the label is linked to the base and there is no phosphate group attached to the sugar molecule. The term "nucleoside" is used herein in its ordinary sense as understood by those skilled in the art. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers.

As used herein, the term "polynucleotide" refers to nucleic acids in general, including DNA (e.g. genomic DNA cDNA), RNA (e.g. mRNA), synthetic oligonucleotides and synthetic nucleic acid analogs. Polynucleotides may include natural or non-natural bases, or combinations thereof and natural or non-natural backbone linkages, e.g. phosphorothioates, PNA or 2'-O-methyl-RNA, or combinations thereof.

As used herein, the term "phasing" refers to phenomena in SBS that is caused by incomplete removal of the 3' terminators and fluorophores, and failure to complete the incorporation of a portion of DNA strands within clusters by polymerases at a given sequencing cycle. Pre-phasing is caused by the incorporation of nucleotides without effective 3' terminators and the incorporation event goes 1 cycle ahead. Phasing and pre-phasing cause the extracted intensities for a specific cycle to consist of the signal of the current cycle as well as noise from the preceding and following cycles. As the number of cycles increases, the fraction of sequences per cluster affected by phasing increases, hampering the identification of the correct base. Pre-phasing can be caused by the presence of a trace amount of unprotected or unblocked 3'-OH nucleotides during sequencing by synthesis (SBS). The unprotected 3'-OH nucleotides could be generated during the manufacturing processes or possibly during the storage and reagent handling processes. Accordingly, the modifications of nucleotide analogues or the linking groups that result in faster SBS cycle time, lower phasing and pre-phasing values, and longer sequencing read length provide greater advantages in SBS applications.

As used herein, the term "protecting moiety" includes, but not limited to molecules that can protect against DNA damages (e.g., photo damage or other chemical damages). Some specific examples include antioxidants, such as vitamin C, vitamin E derivatives, phenolic acid, polyphenols, and derivatives and analogs thereof. It is to be understood that in certain contexts where the term "protecting moiety" is defined, it refers to the moiety resulted from the reaction between one or more functional groups of the protecting moiety with the corresponding functional group of the linker as described herein. For example, when the protecting moiety is "gallic acid," it may refer to the amides and esters of the gallic acid rather than gallic acid itself with the free carboxyl group.

Detectable Labels

Some embodiments described herein relate to the use of conventional detectable labels. Detection can be carried out by any suitable method, including fluorescence spectroscopy or by other optical means. The preferred label is a fluorophore, which, after absorption of energy, emits radiation at a defined wavelength. Many suitable fluorescent labels are known. For example, Welch et al. (*Chem. Eur. J.* 5(3):951-960, 1999) discloses dansyl-functionalised fluorescent moieties that can be used in the present invention. Zhu et al. (*Cytometry* 28:206-211, 1997) describes the use of the fluorescent labels Cy3 and Cy5, which can also be used in the present invention. Labels suitable for use are also disclosed in Prober et al. (*Science* 238:336-341, 1987); Connell et al. (*BioTechniques* 5(4):342-384, 1987), Ansorge et al. (*Nucl. Acids Res.* 15(11):4593-4602, 1987) and Smith et al. (*Nature* 321:674, 1986). Other commercially available fluorescent labels include, but are not limited to, fluorescein, rhodamine (including TMR, texas red and Rox), alexa, bodipy, acridine, coumarin, pyrene, benzanthracene and the cyanins.

Multiple labels can also be used in the present application, for example, bi-fluorophore FRET cassettes (*Tet. Let.* 46:8867-8871, 2000). Multi-fluor dendrimeric systems (*J. Am. Chem. Soc.* 123:8101-8108, 2001) can also be used. Although fluorescent labels are preferred, other forms of detectable labels will be apparent as useful to those of ordinary skill in the art. For example, microparticles, including quantum dots (Empodocles et al., *Nature* 399:126-130, 1999), gold nanoparticles (Reichert et al., *Anal. Chem.* 72:6025-6029, 2000) and microbeads (Lacoste et al., *Proc. Natl. Acad. Sci USA* 97(17):9461-9466, 2000) can all be used.

Multi-component labels can also be used in the present application. A multi-component label is one which is dependent on the interaction with a further compound for detection. The most common multi-component label used in biology is the biotin-streptavidin system. Biotin is used as the label attached to the nucleotide base. Streptavidin is then added separately to enable detection to occur. Other multi-component systems are available. For example, dinitrophenol has a commercially available fluorescent antibody that can be used for detection.

Unless indicated otherwise, the reference to nucleotides is also intended to be applicable to nucleosides. The present application will also be further described with reference to DNA, although the description will also be applicable to RNA, PNA, and other nucleic acids, unless otherwise indicated.

Sequencing Methods

The nucleosides or nucleotides described herein can be used in conjunction with a variety of sequencing techniques. In some embodiments, the process to determine the nucleotide sequence of a target nucleic acid can be an automated process.

The nucleotide analogues presented herein can be used in a sequencing procedure, such as a sequencing-by-synthesis (SBS) technique. Briefly, SBS can be initiated by contacting the target nucleic acids with one or more labeled nucleotides, DNA polymerase, etc. Those features where a primer is extended using the target nucleic acid as template will incorporate a labeled nucleotide that can be detected. Optionally, the labeled nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with an array produced by the methods of the present disclosure are described, for example, in Bentley et al., *Nature* 456: 53-59 (2008), WO 04/018497; WO 91/06678; WO 07/123744; U.S. Pat. Nos. 7,057,026; 7,329,492; 7,211,414; 7,315,019 or 7,405,281, and US Pat. App. Pub. No. 2008/0108082 A1, each of which is incorporated herein by reference.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., *Analytical Biochemistry* 242(1), 84-9 (1996); Ronaghi, *Genome Res.* 11(1), 3-11 (2001); Ronaghi et al. *Science* 281(5375), 363 (1998); U.S. Pat. Nos. 6,210, 891; 6,258,568 and 6,274,320, each of which is incorporated herein by reference). In pyrosequencing, released PPi can be detected by being converted to adenosine triphosphate (ATP) by ATP sulfurylase, and the resulting ATP can be detected via luciferase-produced photons. Thus, the sequencing reaction can be monitored via a luminescence detection system. Excitation radiation sources used for fluorescence based detection systems are not necessary for pyrosequencing procedures. Useful fluidic systems, detectors and procedures that can be used for application of pyrosequencing to arrays of the present disclosure are described, for example, in WIPO Pat. App. Ser. No. PCT/US11/57111, US Pat. App. Pub. No. 2005/0191698 A1, U.S. Pat. Nos. 7,595,883, and 7,244,559, each of which is incorporated herein by reference.

Sequencing-by-ligation reactions are also useful including, for example, those described in Shendure et al. *Science* 309:1728-1732 (2005); U.S. Pat. Nos. 5,599,675; and 5,750,341, each of which is incorporated herein by reference. Some embodiments can include sequencing-by-hybridization procedures as described, for example, in Bains et al., *Journal of Theoretical Biology* 135(3), 303-7 (1988); Drmanac et al., *Nature Biotechnology* 16, 54-58 (1998); Fodor et al., *Science* 251(4995), 767-773 (1995); and WO 1989/10977, each of which is incorporated herein by reference. In both sequencing-by-ligation and sequencing-by-hybridization procedures, nucleic acids that are present in gel-containing wells (or other concave features) are subjected to repeated cycles of oligonucleotide delivery and detection. Fluidic systems for SBS methods as set forth herein, or in references cited herein, can be readily adapted for delivery of reagents for sequencing-by-ligation or sequencing-by-hybridization procedures. Typically, the oligonucleotides are fluorescently labeled and can be detected using fluorescence detectors similar to those described with regard to SBS procedures herein or in references cited herein.

Some embodiments can utilize methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zeromode waveguides. Techniques and reagents for FRET-based sequencing are described, for example, in Levene et al. *Science* 299, 682-686 (2003); Lundquist et al. *Opt. Lett.* 33, 1026-1028 (2008); Korlach et al. *Proc. Natl. Acad. Sci.* USA 105, 1176-1181 (2008), the disclosures of which are incorporated herein by reference.

Some SBS embodiments include detection of a proton released upon incorporation of a nucleotide into an extension product. For example, sequencing based on detection of released protons can use an electrical detector and associated techniques that are commercially available from Ion Torrent (Guilford, CT, a Life Technologies subsidiary) or sequencing methods and systems described in US Pat. App. Pub. Nos. 2009/0026082 A1; 2009/0127589 A1; 2010/0137143 A1; or 2010/0282617 A1, each of which is incorporated herein by reference.

Exemplary Modified Linkers

Additional embodiments are disclosed in further detail in the following examples, which are not in any way intended to limit the scope of the claims.

FIG. 1A illustrates a partial structural formula of a labeled nucleotide 100.

Labeled nucleotide 100 includes a fully functionalized adenosine nucleotide (ffA) 110, a standard linker moiety 115, and a fluorescent dye 120. Standard linker moiety 115 may be a linker moiety typically used in the synthesis of labeled nucleotides for sequencing by synthesis (SBS). In one example, fluorescent dye 120 is NR550S0. In this example, labeled nucleotide 100 may be described as "ffA-NR550S0". In another example, fluorescent dye 120 is SO7181 and the labeled nucleotide 100 may be described as "ffA-SO7181".

Figure 1B:
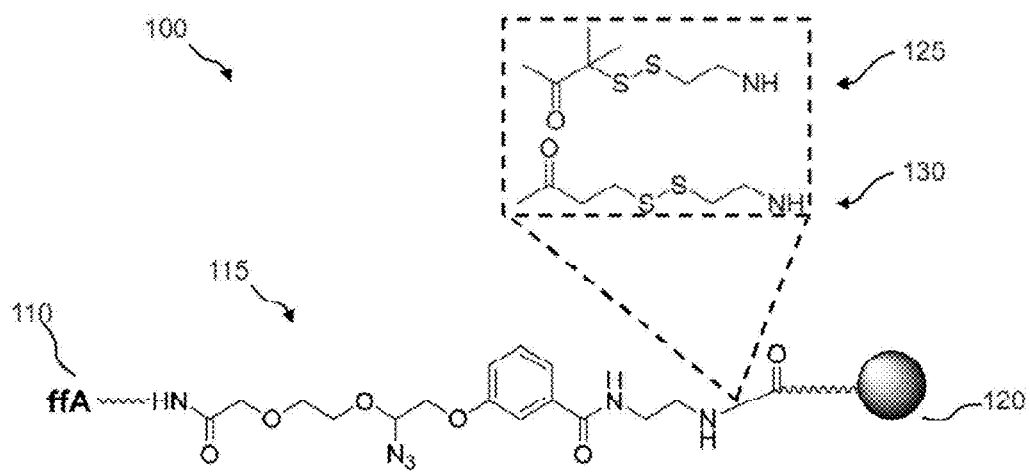
FIG. 1B illustrates the labeled nucleotide of FIG. 1A with two possible linkers 125 and 130 to be inserted into the standard linking group of FIG. 1A.

FIG. 1B illustrates labeled nucleotide 100 of FIG. 1A with two possible structural modifications to standard linker moiety 115. In one example, standard linker moiety 115 includes an AEDI insert 125 between the carbonyl (i.e., —C(=O)—) and the amino (i.e., —NH—) portion of the amido moiety. In this example, the modified labeled nucleotide may be described as "ffA-AEDI-NR550S0". In another example, standard linker moiety 115 includes an SS insert 130 and the modified labeled nucleotide may be designated "ffA-SS-NR550S0".

Figure 2:
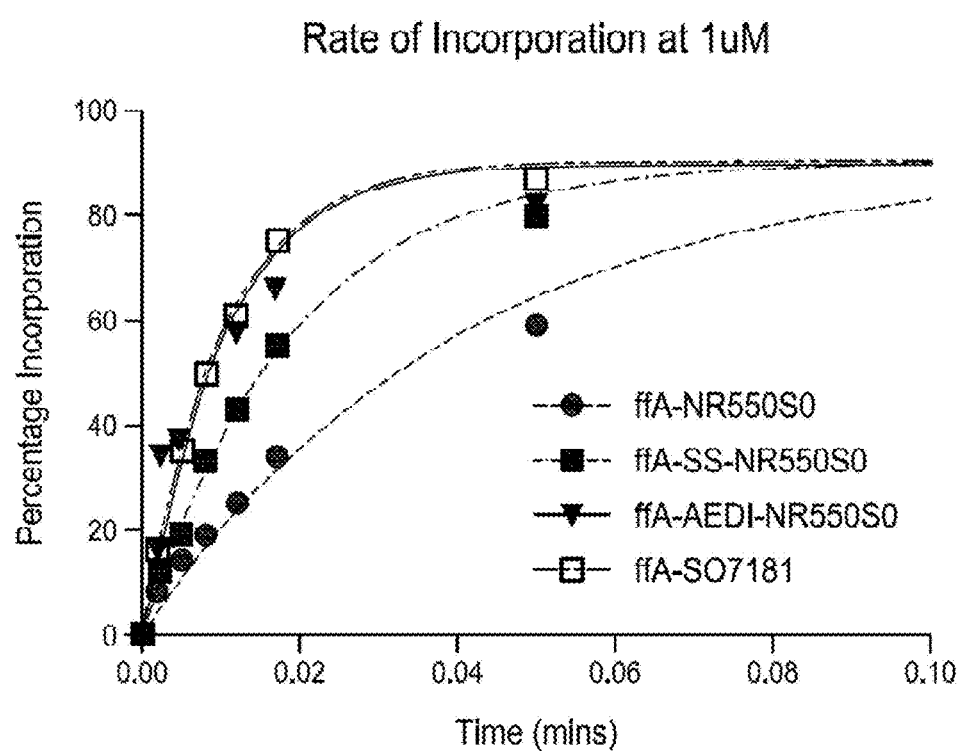
FIG. 2 demonstrates a plot of the nucleotide incorporation rate using the labeled nucleotide of FIG. 1A and the modified labeled nucleotides of FIG. 1B.

FIG. 2 shows a plot of the nucleotide incorporation rate using labeled nucleotide 100 of FIG. 1A and modified labeled nucleotides 100 of FIG. 1B. The assay was carried out at 55° C., in 40 mM ethanolamine (pH 9.8), 9 mM MgCl, 40 mM NaCl, 1 mM EDTA, 0.2% CHAPS with 20 nM primer:template DNA and 30 ug/ml Polymerase 812 (MiSeq Kit V2), 1 mM nucleotide. The enzyme is bound to DNA and then rapidly mixed with nucleotide in a quench flow machine for a short time (up to 10 s) before quenching with 500 mM EDTA. Several time points are taken for each nucleotide. The samples generated are then analyzed on a denaturing gel and the percentage of DNA being converted to DNA+1 is determined and plotted against time to determine the first order rate constant for each nucleotide. The data is summarized in Table 1 below. The data show that the incorporation rate for a labeled nucleotide comprising SS insert 130 (ffa-SS-NR550S0) was about 2 times faster compared to the incorporation rate for a labeled nucleotide comprising a standard linker 115 (ffa-NR550S0). The incorporation rate for a labeled nucleotide comprising an AEDI insert 125 (ffa-AEDI-NR550S0) was about 4 times faster compared to the incorporation rate of ffa-NR550S0. The data also show that the incorporation rate for a labeled nucleotide comprising standard linker 115 and the fluorescent dye SO7181 (ffa-SO7181) was about 4 times faster compared to the incorporation rate of ffa-NR550S0.

TABLE 1

| ffA | K (μM/min) |
| --- | --- |
| ffA-NR550S0 | 22 (1X) |
| ffA-SS-NR550S0 | 54 (2X) |
| ffA-AEDI-NR550S0 | 97 (4X) |
| ffA-SO7181 | 99 (4X) |

FIGS. 3A-3F illustrate the structural formulae of additional inserts 310, 315, 320, 325, 330 and 335 for standard linker moiety 115 of FIG. 1A. In an ACA insert 310, the dimethyl substitutions are removed and the sulfur-sulfur (S—S) bond are replaced with carbon-carbon bond compared to insert 125. The sulfur-sulfur bond is not necessary for SBS (e.g., 2-dye or 4-dye SBS).

In an AcLys insert 315, acetyl protected lysine is used to replace insert 125.

In a BocLys insert 320, tert-butoxycarbonyl protected lysine is used to replace insert 125.

In a dMeO insert 325, the sulfur-sulfur (S—S) bond are replaced with oxygen-carbon (O—CH$_2$) bond compared to insert 125.

In a dMeS insert 330, the sulfur-sulfur (S—S) bond are replaced with sulfur-carbon (S—CH$_2$) bond compared to insert 125.

In a DMP insert 335, the sulfur-sulfur (S—S) bond are replaced with sulfur-carbon (CH$_2$) bond compared to insert 125.

In various examples described herein, inserts including a dimethyl substitution pattern (e.g., AEDI insert 125, dMeO insert 325, and dMeS insert 330) were found to have an increased rate of nucleotide incorporation during SBS.

In various examples described herein, the length of the carbon chains in the inserts may also be varied.

Figure 3A:
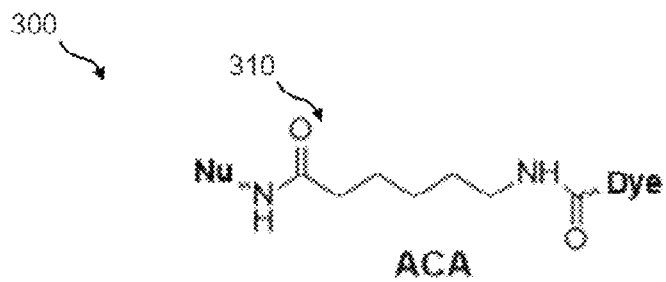
FIGS. 3A-3F illustrate the structural formulae of additional linkers to be inserted into the standard linking group of FIG. 1A.
Figure 3B:
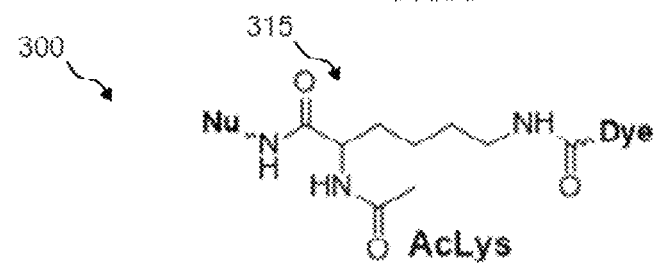
Figure 3C:
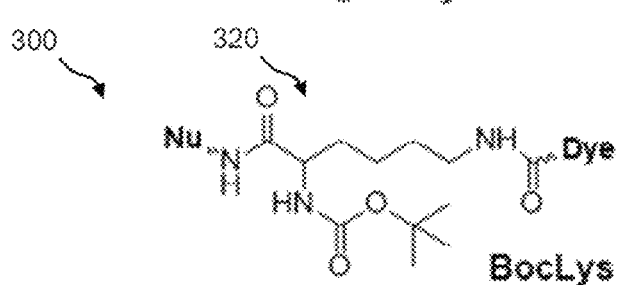
Figure 3D:
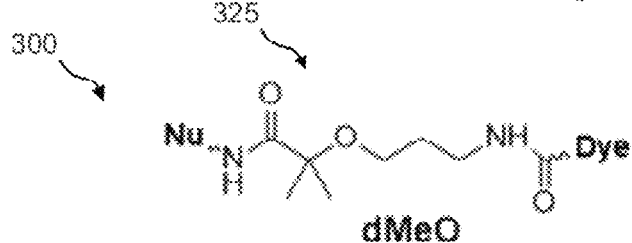
Figure 3E:
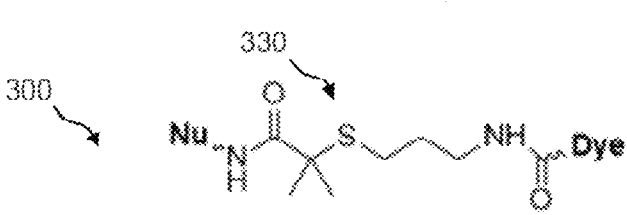
Figure 3F:
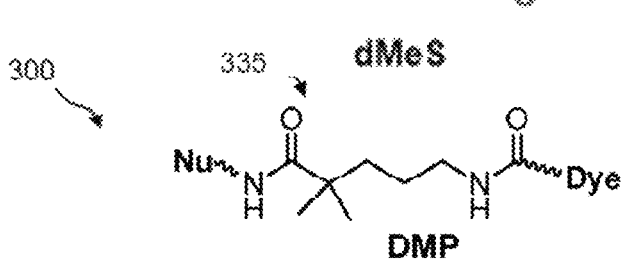

FIG. 4 shows a data table of a two dye sequencing run used to evaluate the effect of AEDI insert 125 of FIG. 1B and AcLys insert 315 of FIG. 3B on sequencing quality. The sequencing was run on a Miseq hybrid platform with Human 550 bp template and 2 times 150 cycles. The new set of dyes, V10/cyan-peg4 A-AEDI550S0, V10/cyan-peg4 A-AcLys550S0, and V10/cyan A-AcLys 550S0 were compared to the standard commercial dye set V4 and an improved dye set of Nova platform V5.75. For each of V10/cyan-peg4 A-AEDI550S0, V10/cyan-peg4 A-AcLys550S0, and V10/cyan A-AcLys 550S0 samples, the phasing value (Ph R1) was lower than the phasing values of samples without the AEDI or AcLys inserts. Therefore, labeled nucleotides comprising additional inserts 125 and 315 demonstrated improvements in sequencing quality.

Figure 5A:
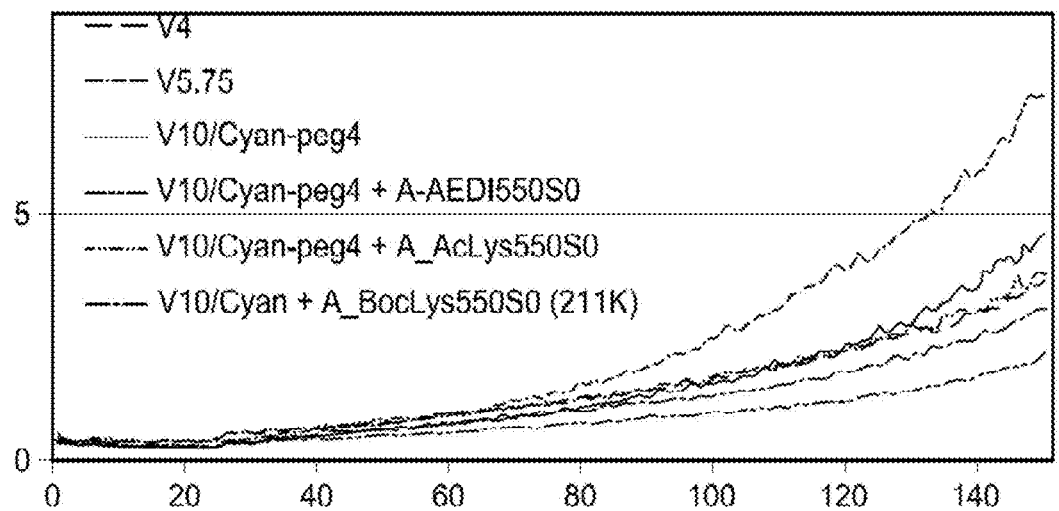
FIGS. 5A and 5B show a plot of error rate for read 1 and a plot of error rate for read 2 of the sequencing run of FIG. 4 using linkers insert 125 and 315.
Figure 5B:
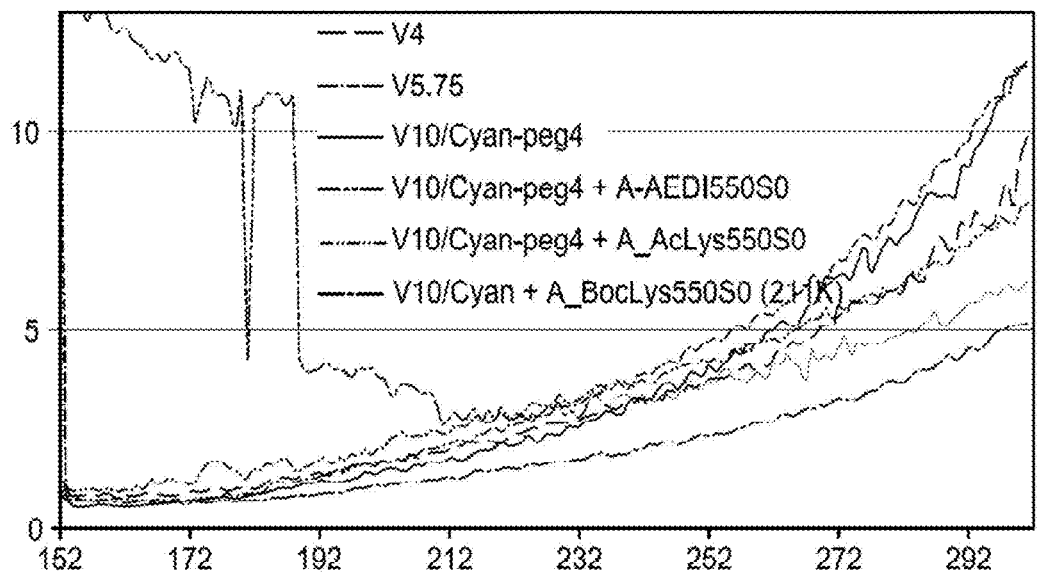

FIGS. 5A and 5B show a plot of error rates for read 1 and a plot of error rates for read 2 of the sequencing run of FIG. 4 respectively. For read 1, the error rates of V10/cyan-peg4 A-AEDI550S0 and V10/cyan-peg4 A-AcLys550S0 were lower than the same set of dye V10/Cyan-peg4 without the insert. For read 2, it is even more pronounced when AcLys insert 315 is used, where the final error rate was reduced by 30% compare to the no-insert dye set. Therefore, inserts 125 and 315 have proven to improve the sequencing quality significantly.

FIG. 6 shows a data table of a sequencing run used to evaluate the effect of AEDI insert 125 and ACA insert 310 on sequencing quality. The sequencing was run on a Miseq hybrid platform with Human 550 bp template and 2 times 150 cycles. The new set of dyes, V10/cyan-peg4 A-AEDI550S0, V10/cyan-peg4 A-ACALys550S0, were compared to the standard commercial dye set V4 and an improved dye set of Nova platform V5.75. Again, each of V10/cyan-peg4 A-AEDI550S0 and V10/cyan-peg4 A-ACA550S0 samples has a lower phasing value (Ph R1) compared to samples without the AEDI or ACA inserts and thus showed improvement in sequencing quality.

Figure 7A:
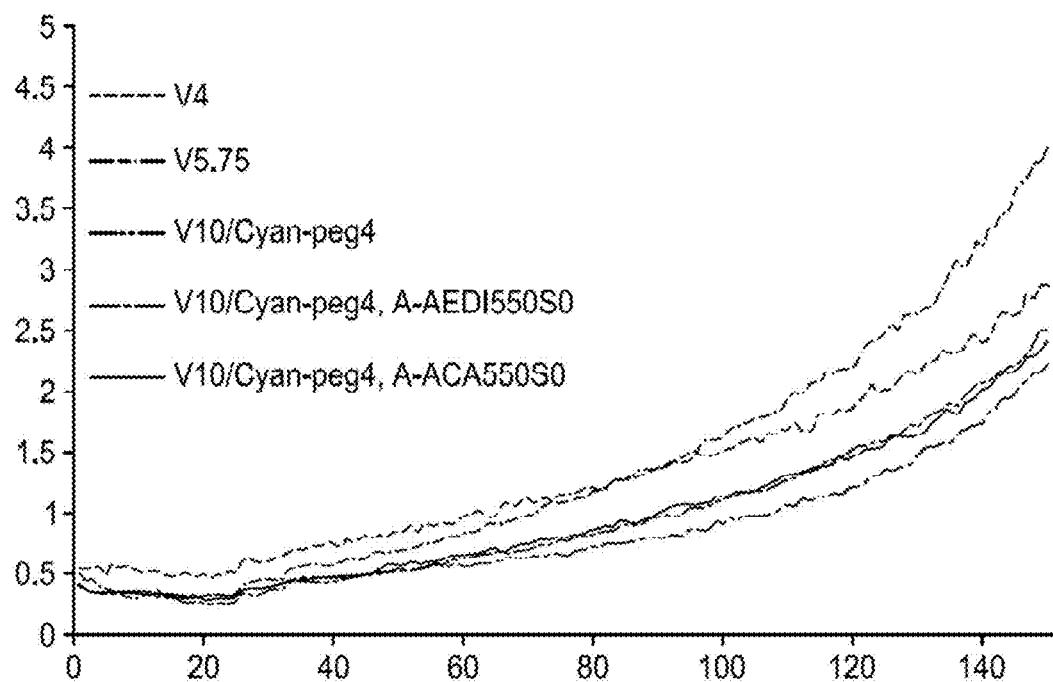
FIGS. 7A and 7B show a plot of error rate for read 1 and a plot of error rate for read 2 of the sequencing run of FIG. 6 using linker insert 125.
Figure 7B:
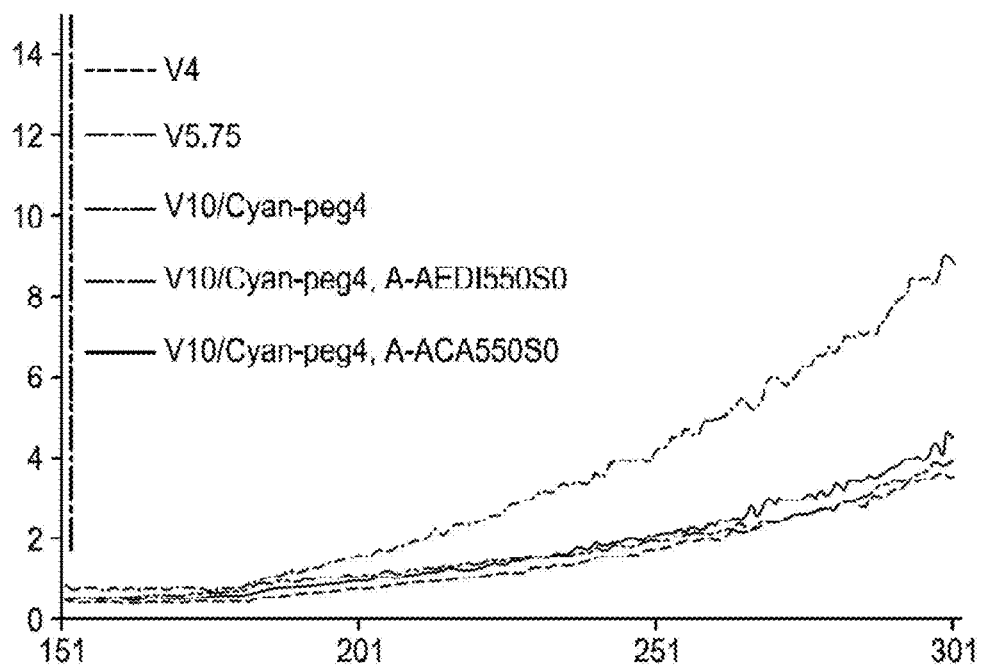

FIGS. 7A and 7B show a plot of error rates for read 1 and a plot of error rates for read 2 of the sequencing run of FIG. 6 respectively. The error rates for read 1 for the set comprising the new insert AEDI (V10/cyan-peg4 A-AEDI55050), was lower than the same set of dye without the insert, V10/Cyan-peg4. The insert ACA (V10/Cyan-peg4 ACA55050) gave a similar error rate plot in both read to the standard V10/Cyan-peg4. AEDI showed again to improve the quality of sequencing. Those data showed also the structure of insert itself is having an influence on the improvement of the sequencing quality.

Figure 8A:
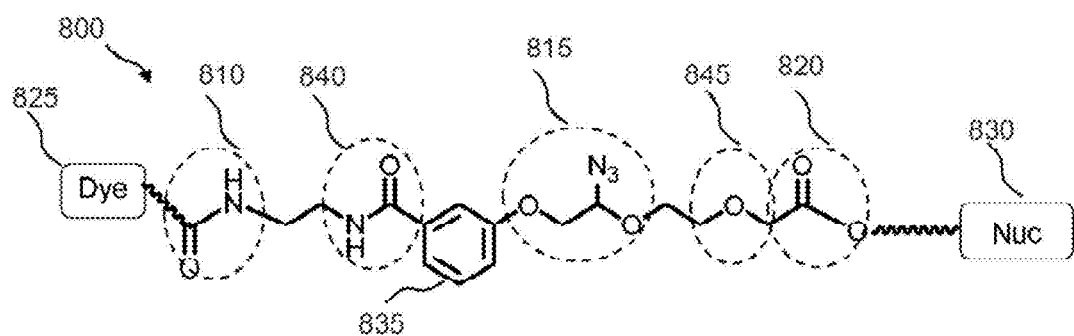
FIG. 8A shows an example of a standard $LN_3$ linker structure.
Figure 8B:
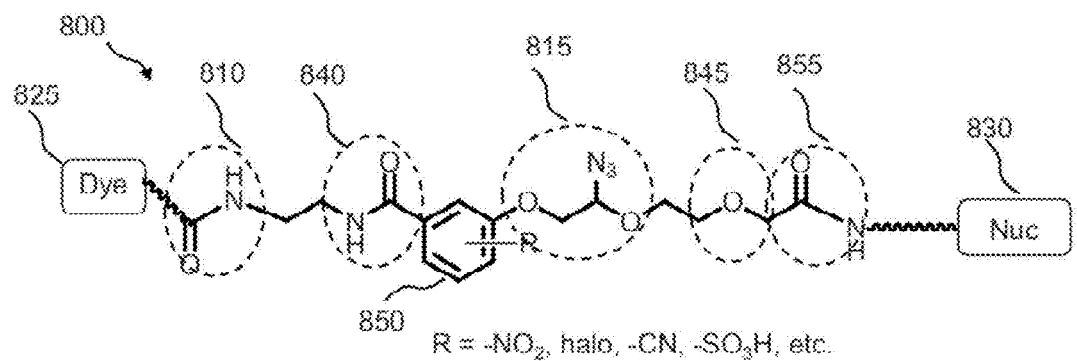
FIGS. 8B, 8C and 8D show three examples of modified structures of the $LN_3$ linker of FIG. 8A.

FIG. 8A shows the structural formula of a standard LN$_3$ linker 800. LN$_3$ linker 800 includes a first substituted amido functional moiety 810, a second azido-substituted PEG functional moiety 815, and a third ester functional moiety 820 that may be desired in a linker structure for linking a dye molecule 825 to a nucleotide 830. First functional moiety 810 may, for example, be used to attach dye molecule 825 to LN$_3$ linker 800. Second functional moiety 815 may, for example, be a cleavable functional group that may be used to cleave dye molecule 825 from LN$_3$ linker 800. Third functional moiety 820 may, for example, be used to attach nucleotide 830 to LN$_3$ linker 800. FIG. 8B illustrates some modification to the standard LN$_3$ linker where the phenoxy moiety 850 is substituted with one to four substituents selected from —NO$_2$, —CN, halo or —SO$_3$H. In addition, the ester moiety 820 is replaced with an amido moiety 855.

Figures 9A, 9B:
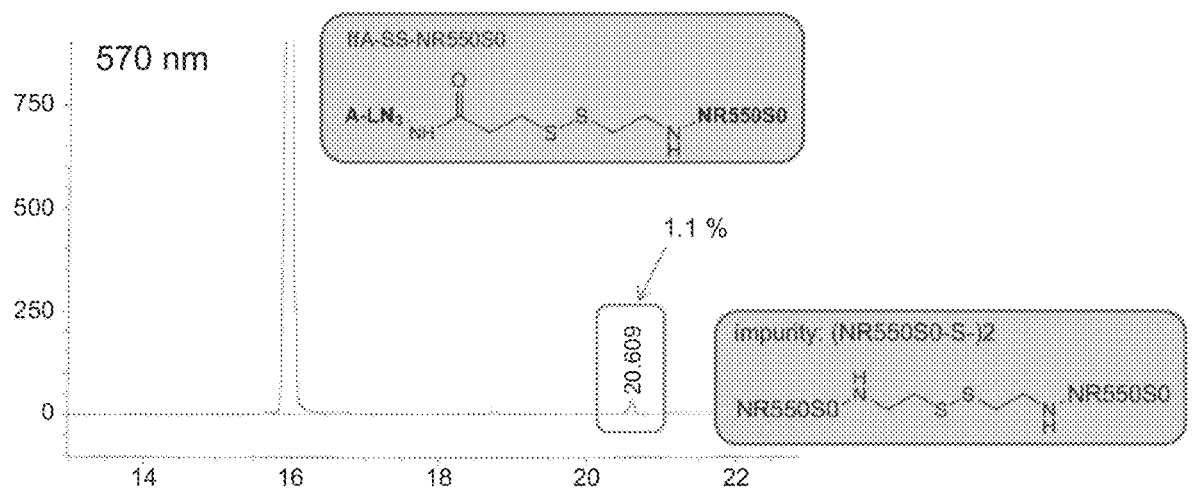
FIG. 9A is a chromatogram showing the appearance of an impurity in an ffA with SS-linker.
FIG. 9B is a table comparing the stability of ffAs with SS-linker and AEDI-linker.
Figure 9C:
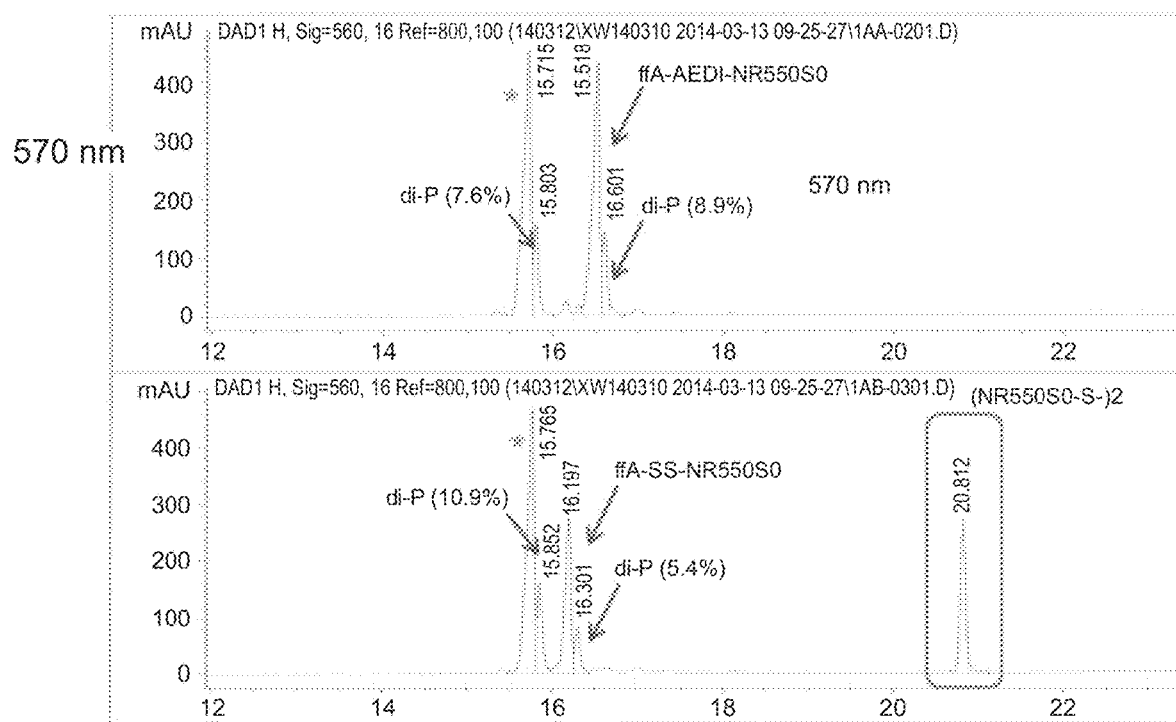
FIG. 9C is a chromatogram showing a comparison of SS-linker and AEDI-linker ffAs in IMX 60° for 22 hours, again showing an impurity with the SS linker.

FIG. 9A is a graph showing the appearance of an impurity in an ffA with SS-linker. With ffA-SS-NR550S0 after HPLC purification: impurity appeared overnight in a slightly basic condition (pH8-9). R.t. overnight in 0.1M TEAB/CH3CN. FIG. 9B compares the stability of ffAs with SS-linker and AEDI-linker, with the AEDI-linker showing significantly improved stability compared to SS linkers. ffA-LN3-NR550S0 was used as internal reference. The disulfide side product: (NR550S0-S-)2. FIG. 9C shows a comparison of SS-linker and AEDI-linker ffAs in IMX 60° for 22 hours, again showing an impurity with the SS linker. The internal control is ffA-LN3-NR550S0. Di-P: diphosphate.

Figures 10A, 10B:
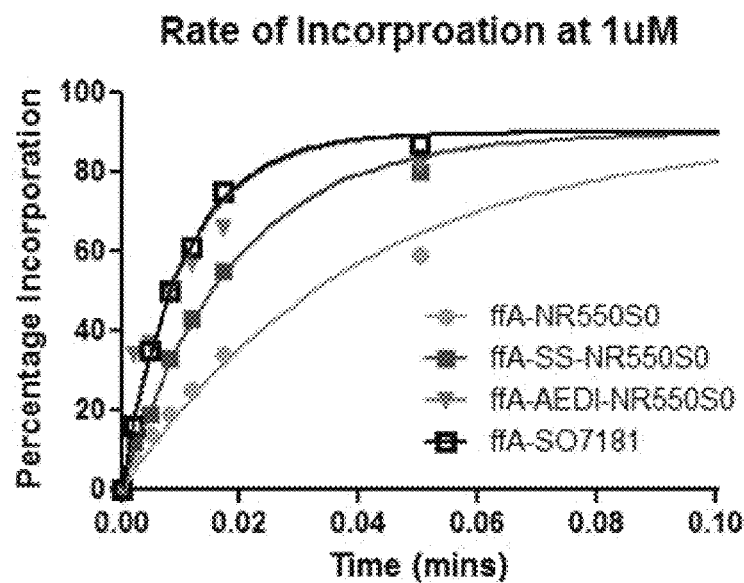
FIGS. 10A, 10B and 10C show the unexpected increase of nucleotide incorporation speed in solution with linker changes.
Figure 10C:
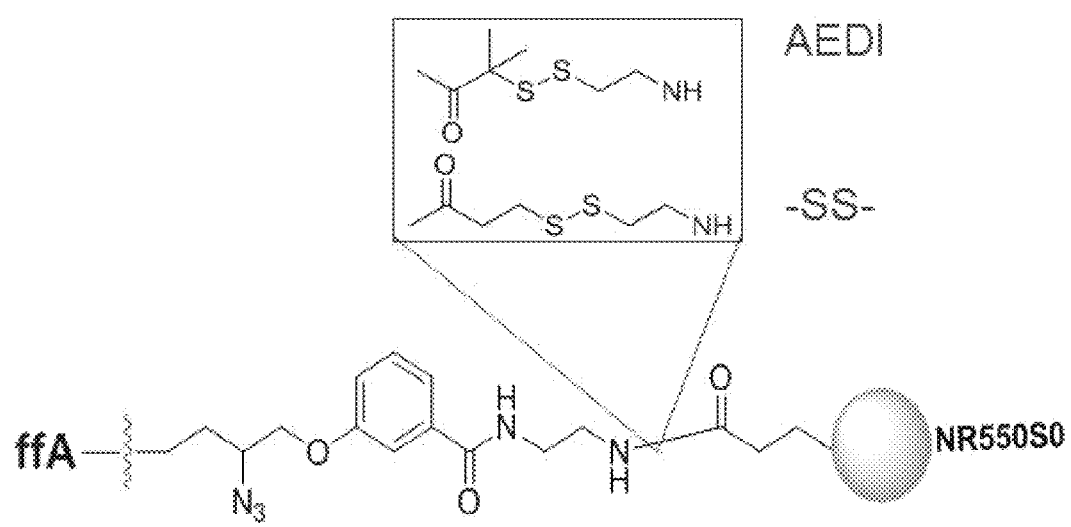

FIGS. 10A, 10B and 10C show the unexpected increase of nucleotide incorporation speed in solution with linker changes. FIG. 10A shows the rate of incorporation at luM. The results show that the dye and linker had a significant effect on incorporation kinetics with FIG. 10B clearly showing the benefit of the AEDI linker in incorporation kinetics. FIG. 10C diagrammatically shows the AEDI and SS linkers with NR550S0.

Figure 11A:
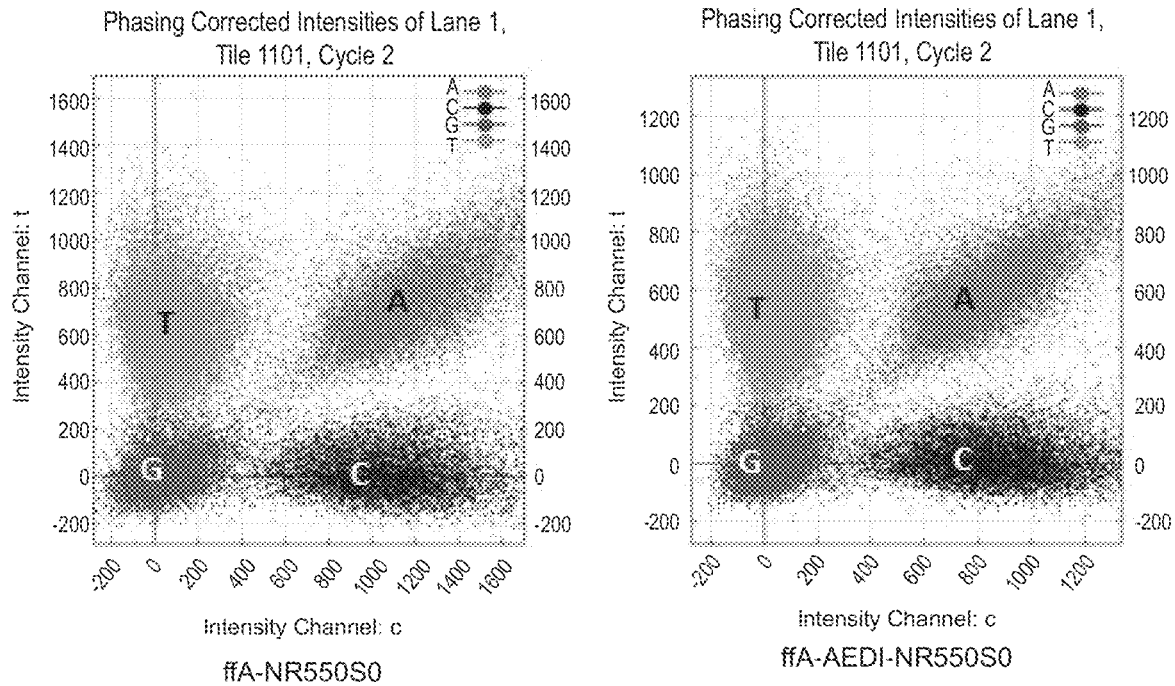
FIG. 11A shows scatter plots for V10 combinations with different A-550S0 (same concentration).
Figure 11A:
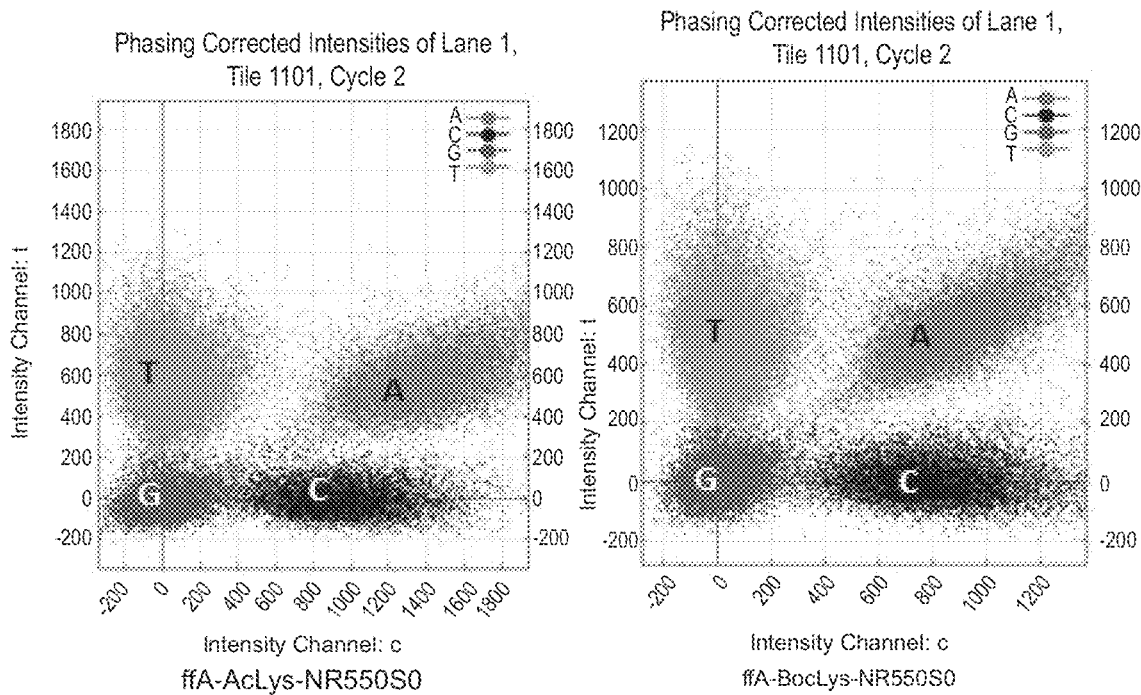
Figure 11B:
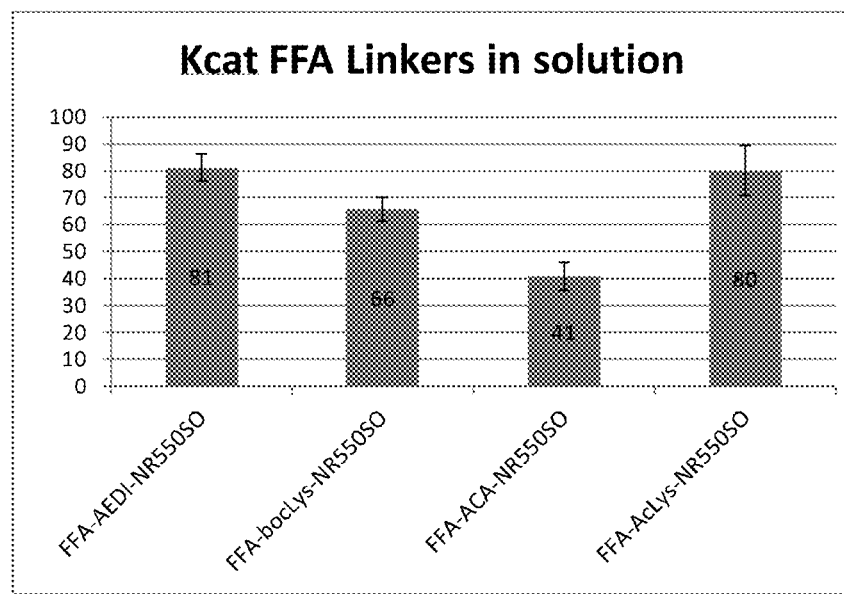
FIG. 11B shows Kcat FFA Linkers in solution.

FIG. 11A shows scatter plots for V10 combinations with different A-550S0 (same concentration). Scatter plots are for tile 1 cycle 2. FIG. 11B shows Kcat FFA Linkers in solution. It can be seen that on surface in terms of incorporation rate the AEDI linker is faster than no linker: 'A'-cloud (on the scatter plot) slightly moving towards center. AcLys linker is slower than AEDI and no linker: 'A'-cloud moving towards x axis. BocLys linker looks similar to no linker and not far from the AEDI linker. In solution it can be seen that the ACA-linker was slowest, whilst AEDI and ACLys have similar Kcat, followed by BocLys.

Figure 12B:
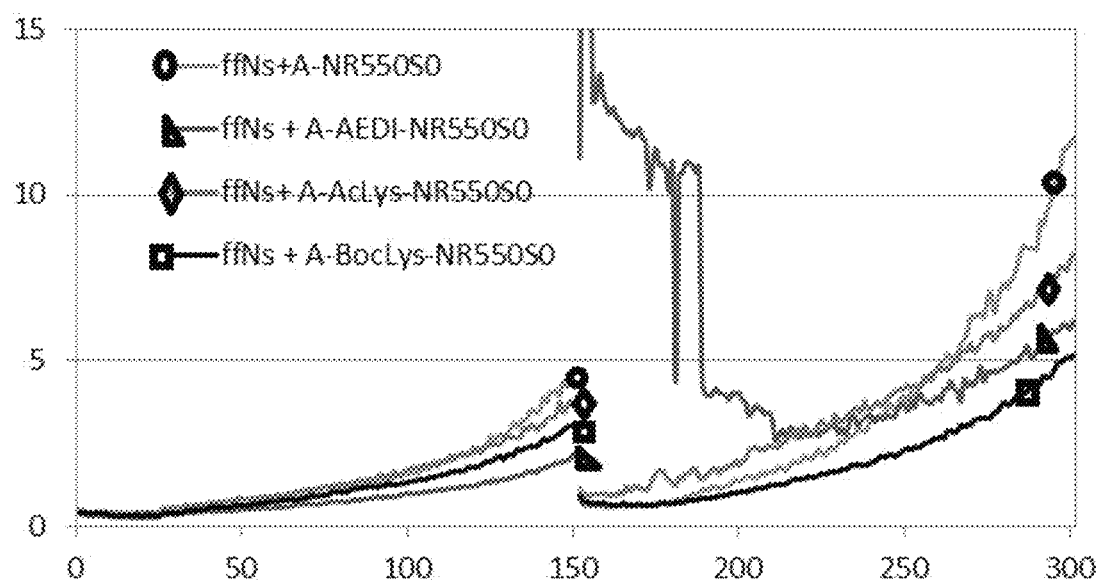

FIGS. 12A and 12B show sequencing metrics on M111, Human550, 2×151 cycles. Use ffNs in combination with different A-550S0 (same concentration). It can be seen that both AEDI and BocLys linker gave similar good sequencing results. Although the solution Kcat of AEDI and AcLys are similar, the sequencing result of AEDI is slightly better.

Figure 8C:
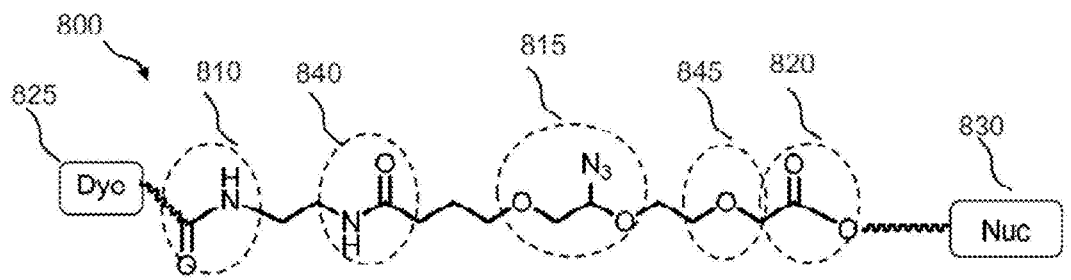
Figure 8D:
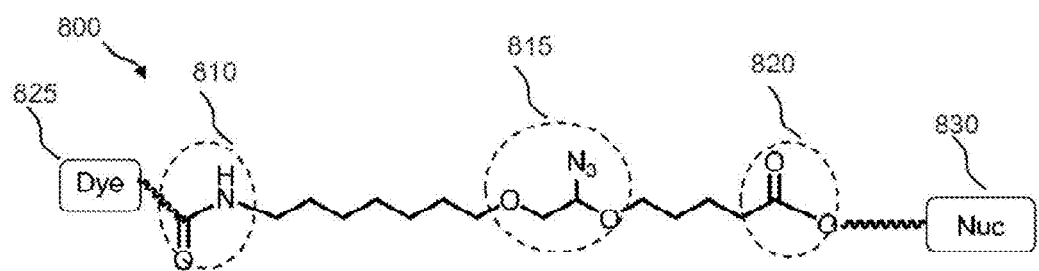

LN$_3$ linker 800 includes an optional phenoxy moiety 835 that may be removed from LN$_3$ linker 800 as shown in FIG. 8C. LN$_3$ linker 800 also includes an optional amido moiety 840 and an optional ether moiety 845, both of which may be removed from LN$_3$ linker 800 as shown FIG. 8D. The purpose to remove certain functional groups like amido moiety 810, phenoxy moiety 835 is to test if they have negative interactions with the enzyme during the nucleotide incorporation, which might reduce the incorporation efficiency.

Figure 8E:
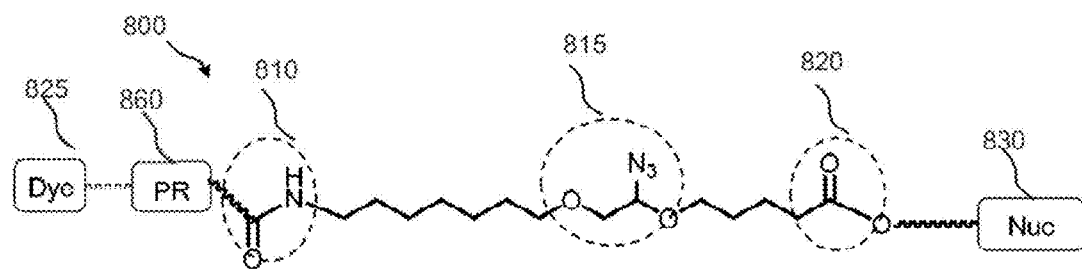
FIG. 8E illustrates the insertion of a protecting moiety into the linker FIG. 8D.

FIG. 8E illustrates the insertion or addition of a protecting moiety 860 into the linker. Protecting moiety 860 is inserted between functional moiety 810 (or can be attached to the phenoxy moiety 835 or 850 in FIGS. 8A-8C) and dye molecule 825. Protecting moiety 860 may, for example, be a molecule that protects against DNA damage. DNA damage including photo damage or other chemical damages is one of the cumulative effects (i.e., cycle by cycle) of SBS. Substantially reducing or eliminating DNA damage may provide for more efficient SBS and longer sequencing reads. In some embodiments, protecting moiety 860 can be selected from a triplet state quencher such as Trolox, gallic acid, 2-mercaptoethanol (BME), etc. In some other embodiments, protecting moiety 860 can be selected from quenching or protective reagent such as 4-nitrobenzyl alcohol or a salt of ascorbic acid, such as sodium ascorbate. In some other embodiments, a protecting agent can be physically mixed into the buffer rather than forming covalent bonding with the labeled nucleoside or nucleotide. However, this approach may require higher concentration of the protecting agent and may be less efficient. As an alternative, protecting moiety covalently attached to the nucleosides or nucleotides may provide better protection against DNA damage. In some further embodiments of FIGS. 8C, 8D and 8E, the ester moiety 820 can also be replaced with the amido moiety 855 and the phenoxy moiety 835 be further substituted.

In any of the examples demonstrated in FIG. 8A-8E, AEDI insert 125 and SS insert 130 of FIG. 1B and inserts 300 of FIGS. 3A-3F may, for example, be inserted between first functional moiety 810 and dye molecule 825 of linker 800.

EXAMPLES

Additional embodiments are disclosed in further detail in the following examples, which are not in any way intended to limit the scope of the claims.

General Reaction Procedure for Preparing ffA-LN$_3$-AEDI-NR550S0:

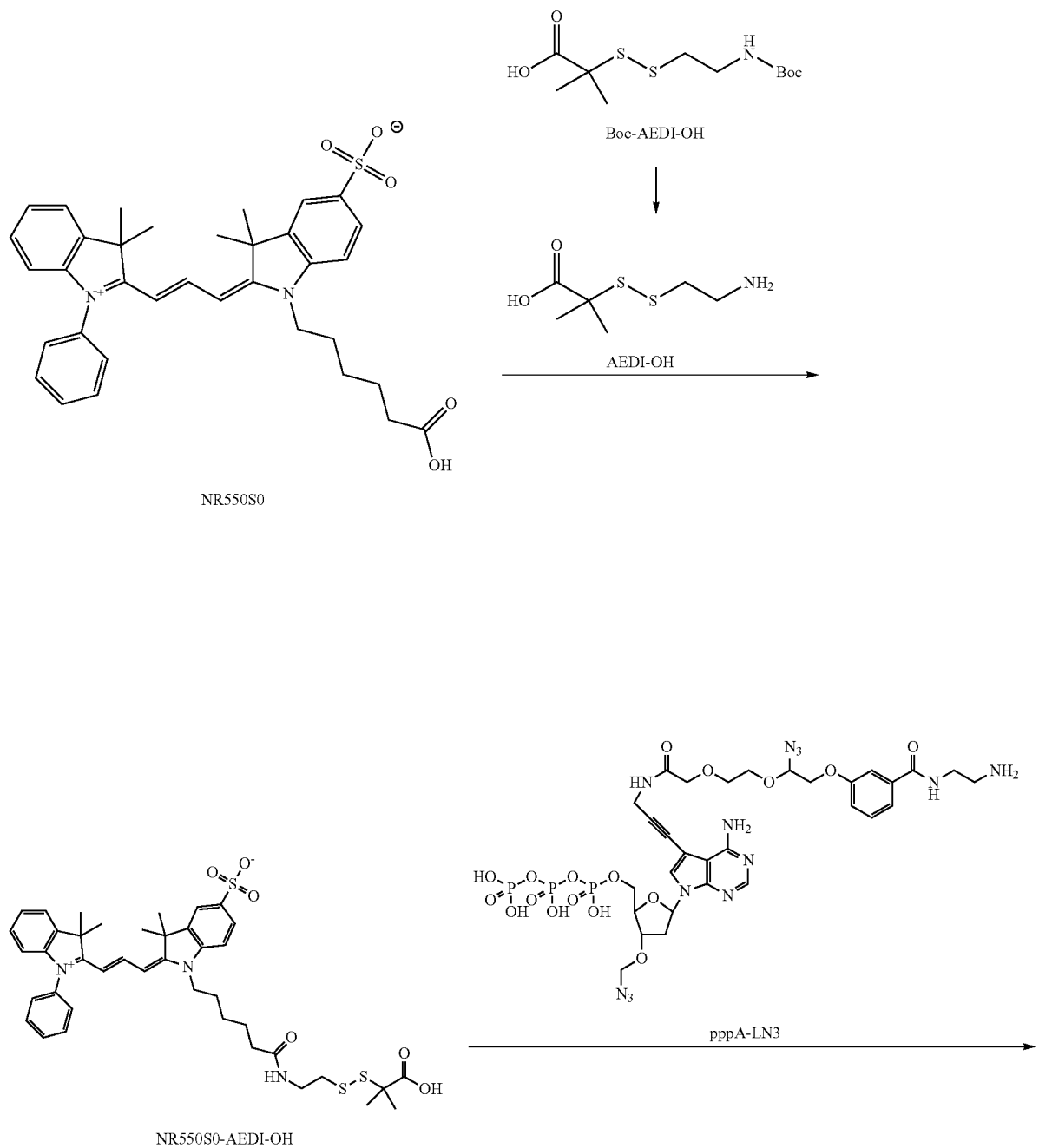

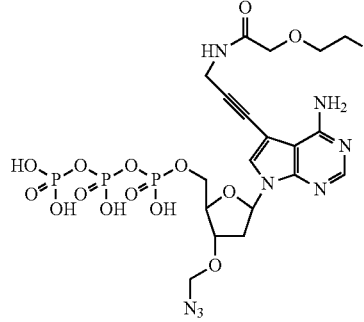

ffA-LN3-AEDI-NR550S0

In a 50 ml round-bottom flask, Boc-AEDI-OH (1 g, 3.4 mmol) was dissolved in DCM (15 ml) and TFA (1.3 ml, 17 ml) was added to the solution at rt. The reaction mixture was stirred for 2 hours. TLC (DCM:MeOH=9:1) indicated complete consumption of Boc-AEDI-OH. The reaction mixture was evaporated to dryness. TEAB (2 M, ~15 ml) was then added to the residue and pH was monitored until to neutral. The mixture was then dissolved in $H_2O/CH_3CN$ (1:1, ~15 ml) and evaporated to dryness. The procedure was repeated for 3 times to remove excess of TEAB salt. The white solid residue was treated with $CH_3CN$ (20 ml) and stirred for 0.5 hour. Filtrated off the solution and washed the solid with $CH_3CN$, pure AEDI-OH-TFA salt was obtained (530 mg, 80%). $^1$H NMR (400 MHz, $D_2O$, δ(ppm)): 3.32 (t, J=6.5 Hz, 2H, $NH_2$—$CH_2$); 2.97 (t, J=6.5 Hz, 2H, S—$CH_2$); 1.53 (s, 6H, 2×$CH_3$). $^{13}$C NMR (400 MHz, $D_2O$, δ(ppm)): 178.21 (s, CO); 127.91, 117.71 (2 s, TFA); 51.87 (s, C—$(CH_3)_2$); 37.76 (t, $CH_2$—NH2); 34.23 (t, S—$CH_2$); 23.84 (q, 2×$CH_3$). $^{19}$F NMR (400 MHz, $D_2O$, δ(ppm)): −75.64.

In a 50 ml round-bottom flask, dye NR550S0 (114 mg, 176 umol) was dissolved in DMF (anhydrous, 20 mL) and evaporated to dry. The procedure was repeated for 3 times. Anhydrous DMA (10 mL) and Hunig's base (92 µL, 528 µmol, 3 equivalents) was then pipetted into the round bottom flask. TSTU (69 mg, 228 umol, 1.3 equivalents) was added in one portion. The reaction mixture was kept at rt. After 30 min, TLC ($CH_3CN:H_2O$=85:15) analysis indicated that the reaction completed. AEDI-OH (68 mg, 352 µmol, 2 equivalents) in 0.1 M TEAB was added to the reaction mixture and stirred at rt for 3 h. TLC ($CH_3CN:H_2O$=8:2) showed complete consumption of the activated ester and a red spot appeared below the activated ester. Meanwhile, the analytic HPLC also indicated complete consumption of the activated ester and formation of the product. The reaction was quenched with TEAB buffer (0.1M, 10 ml) and the volatile solvent was removed by by reduced pressure evaporation (HV) and purified on Axia column to obtain NR550S0-AEDI-OH. Yield: 60%.

In a 25 ml round-bottom flask, NR550S0-AEDI-OH (10 umol) was dissolved in DMF (anhydrous, 5 mL) and evaporated to dry. The procedure was repeated for 3 times. Anhydrous DMA (5 mL) and DMAP (1.8 mL, 15 µmol, 1.5 equivalents) was then added into the round bottom flask. DSC (5.2 mg, 20 µmol, 2 equivalents) was added in one portion. The reaction mixture was kept at room temperature. After 30 min, TLC ($CH_3CN:H_2O$=8:2) analysis indicated that the reaction completed. Hunig's Base (3.5 ul, 20 umol) was pippeted in to the reaction mixture. Then a solution of pppA-$LN_3$ (20 µmol in 0.5 ml $H_2O$, 2 equivalent) and $Et_3N$ (5 ul) was added to the reaction mixture and stirred at rt over-night. TLC ($CH_3CN:H_2O$=8:2) showed complete consumption of the activated ester and a red spot appeared on the baseline. Meanwhile, the analytic HPLC also indicated complete consumption of the activated ester and formation of the final product. The reaction was quenched with TEAB buffer (0.1M, 10 ml) and loaded on a DEAE Sephadex column (25 g Biotage column). The column was eluted with gradient as shown in Table 2 below.

A: 0.1 M TEAB buffer (10% $CH_3CN$)

B: 1 M TEAB buffer (10% $CH_3CN$).

Gradient:

TABLE 2

| STEP | Solvents Mix (B%) | Length (ml) |
|---|---|---|
| 1 | 0 | 100 |
| 2 | 0-45 | 50 |
| 3 | 45 | 100 |
| 4 | 45-100 | 50 |
| 5 | 100 | 100 |

The desired product was eluted out from 45% to 100% 1 M TEAB buffer. The fraction containing the product were combined, evaporated and purified by HPLC (YLC column, 8 ml/min). Yield: 53%.

In summary, the present invention may relate to a nucleoside or nucleotide covalently attached to a fluorophore through a linker, wherein said linker comprises a structure of formula (I) or (II), or combination of both:

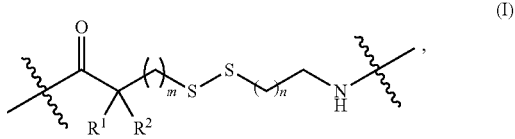

(I)

-continued

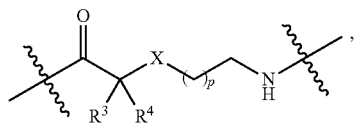
(II)

each R[1] and R[2] is independently selected from hydrogen or optionally substituted $C_{1-6}$ alkyl;

R[3] is selected from hydrogen, optionally substituted $C_{1-6}$ alkyl, —NR[5]—C(=O)R[6], or —NR[7]—C(=O)—OR[8];

R[4] is selected from hydrogen or optionally substituted $C_{1-6}$ alkyl;

each R[5] and R[7] is independently selected from hydrogen, optionally substituted $C_1$-6 alkyl, optionally substituted phenyl, or optionally substituted $C_{7-12}$ aralkyl;

each R[6] and R[8] is independently selected from optionally substituted $C_{1-6}$ alkyl, optionally substituted phenyl, optionally substituted $C_{7-12}$ aralkyl, optionally substituted $C_{3-7}$ cycloalkyl, or optionally substituted 5 to 10 membered heteroaryl;

each of the methylene repeating unit in

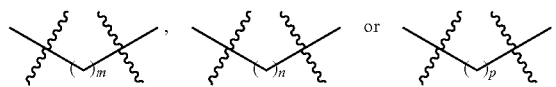

is optionally substituted;

X is selected from methylene ($CH_2$), oxygen (O), or sulfur (S);

m is an integer of 0 through 20;

n is an integer of 1 through 20; and p is an integer of 1 through 20, provided that the fluorophore labeled nucleoside or nucleotide does not have the structure:

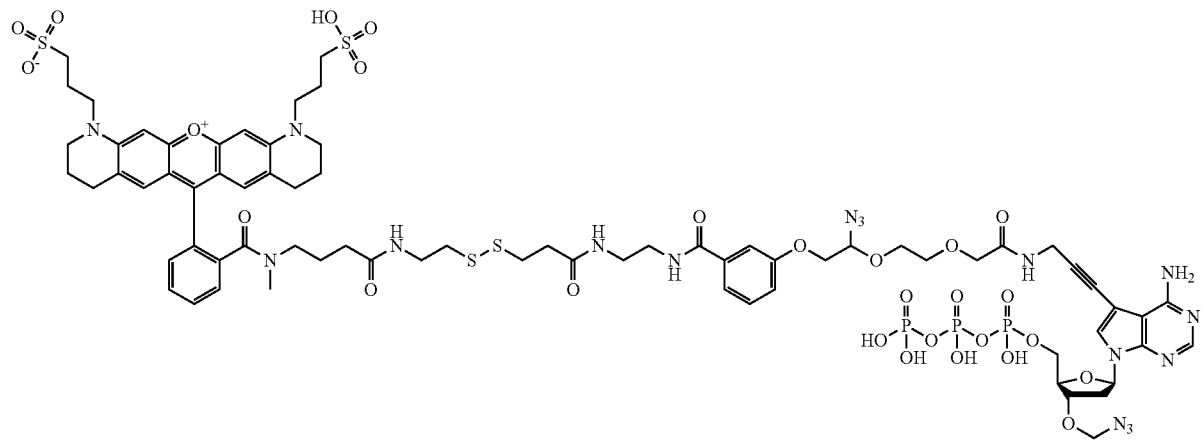

In some cases the nucleoside or nucleotide referenced above, the structure of formula (I) is also represented by formula (Ia) or (Ib):

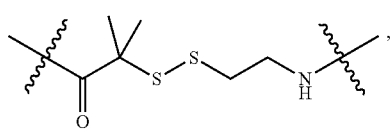
(Ia)

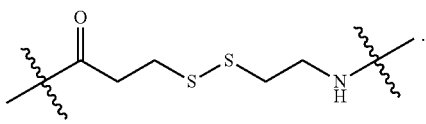
(Ib)

Further, the structure of formula (II) may also be represented by formula (IIa), (IIb), (IIc), (IId), (IIe) or (IIf):

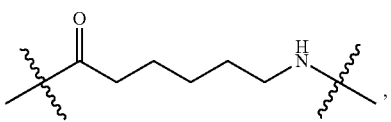
(IIa)

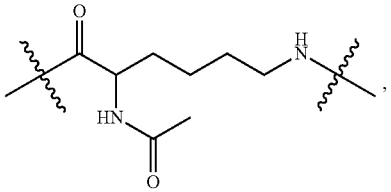
(IIb)

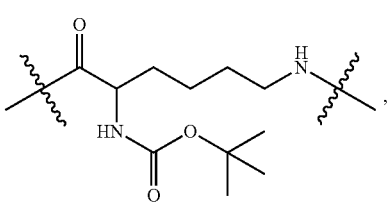
(IIc)

-continued

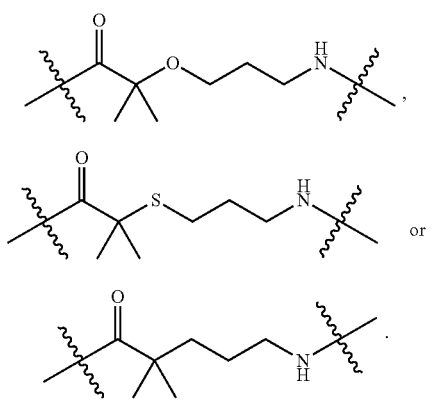

More particularly, the present invention may relate to a nucleoside or nucleotide covalently attached to a fluorophore through a linker, wherein said linker comprises a structure of formula (I) or (II), or combination of both:

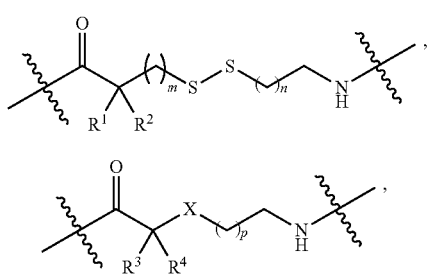

wherein
$R^1$ is selected from optionally substituted $C_{1-6}$ alkyl;
$R^2$ is selected from hydrogen or optionally substituted $C_{1-6}$ alkyl;
$R^3$ is selected from optionally substituted $C_{1-6}$ alkyl, $-NR^5-C(=O)R^6$, or $-NR^7-C(=O)-OR^8$;
$R^4$ is selected from hydrogen or optionally substituted $C_{1-6}$ alkyl;
each $R^5$ and $R^7$ is independently selected from hydrogen, optionally substituted $C_{1-6}$ alkyl, optionally substituted phenyl, or optionally substituted $C_{7-12}$ aralkyl;
each $R^6$ and $R^8$ is independently selected from optionally substituted $C_{1-6}$ alkyl, optionally substituted phenyl, optionally substituted $C_{7-12}$ aralkyl, optionally substituted $C_{3-7}$ cycloalkyl, or optionally substituted 5 to 10 membered heteroaryl;
each of the methylene repeating unit in

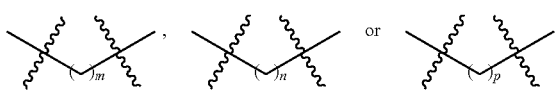

is optionally substituted;
X is selected from methylene ($CH_2$), oxygen (O), or sulfur (S);
m is an integer of 0 through 20;
n is an integer of 1 through 20; and
p is an integer of 1 through 20.

It is preferred that the structure of formula (I) is also represented by formula (Ia):

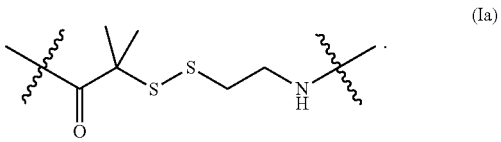 [SMILES: *NCCSSC(C)(C)C(*)=O]

Further, the structure of formula (II) is also represented by formula (IIb), (IIc), (IId), (IIe) or (IIf):

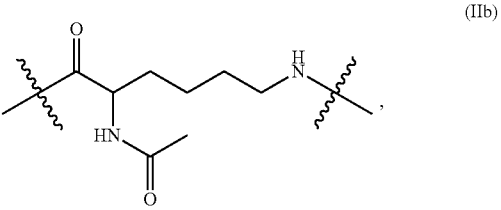

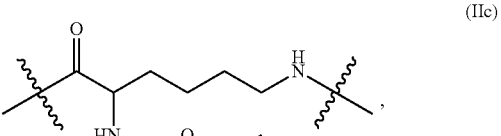

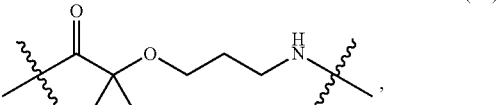

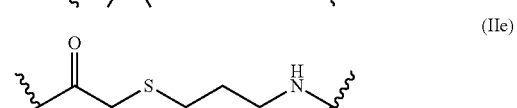

What is claimed is:
1. A nucleotide covalently attached to a fluorophore through a linker comprising the following structure:

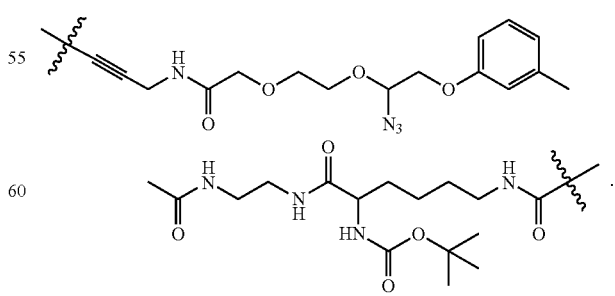

2. The nucleotide of claim 1, wherein the nucleotide is a nucleotide triphosphate.

3. The nucleotide of claim 2, wherein the nucleotide has a T base.

4. The nucleotide of claim 2, wherein the nucleotide has a C base.

5. The nucleotide of claim 2, wherein the nucleotide has an A base.

6. The nucleotide of claim 2, wherein the nucleotide comprises the following structure:

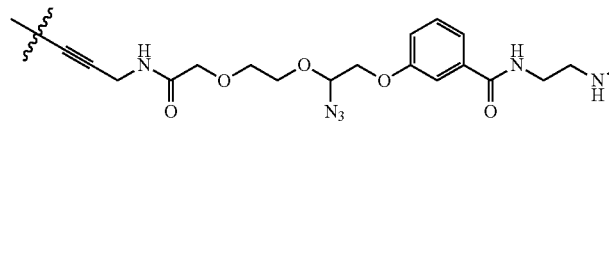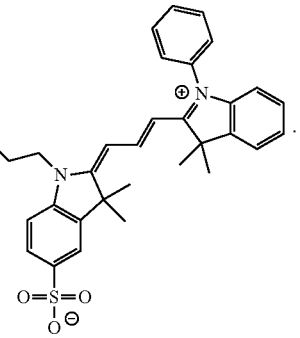

7. The nucleotide of claim 2, wherein the nucleotide comprises a deoxyribose and a 3' blocking group.

8. The nucleotide of claim 7, wherein the nucleotide has a 3' azidomethyl blocking group attached to the 3' oxygen of the deoxyribose.

9. The nucleotide of claim 6, wherein the nucleotide comprises deoxyribose and a 3' azidomethyl blocking group attached to the 3' oxygen of the deoxyribose.

10. A polynucleotide comprising a nucleotide of claim 7 incorporated therein.

11. The polynucleotide of claim 10, wherein the incorporated nucleotide comprises a 3' azidomethyl blocking group attached to the 3' oxygen of the deoxyribose.

12. A kit comprising a nucleotide according to claim 7.

13. The kit of claim 12, wherein the nucleotide comprises the following structure:

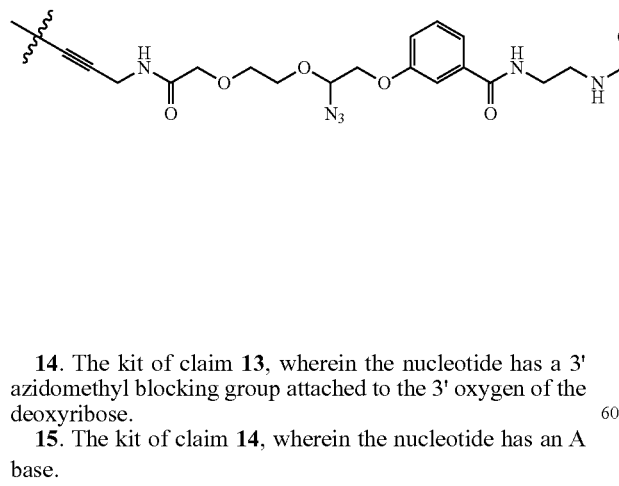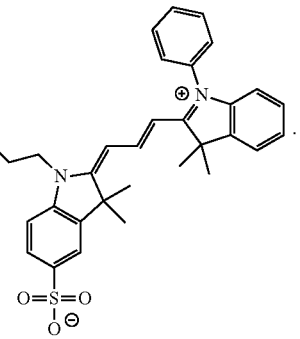

14. The kit of claim 13, wherein the nucleotide has a 3' azidomethyl blocking group attached to the 3' oxygen of the deoxyribose.

15. The kit of claim 14, wherein the nucleotide has an A base.

16. The kit of claim 14, wherein the nucleotide has a T base.

17. The kit of claim 14, wherein the nucleotide has a C base.

18. A method of sequencing an array of target nucleic acids, comprising:

contacting a solid support comprising an array of immobilized target nucleic acids with one or more different types of nucleotides A, C, G and T in the presence of a DNA polymerase, wherein each of the one or more different types of nucleotides comprises a 3' blocking group, and wherein at least one type of nucleotide is the nucleotide according to claim 8;

incorporating one type of nucleotides into primers complementary to the target nucleic acids, which are at least partially hybridized to the target nucleic acids;

detecting fluorescent signals from the incorporated nucleotides to determine the identity of the incorporated nucleotides.

19. The method of claim 18, wherein each of the one or more different types of nucleotides comprises a 3' azidomethyl blocking group attached to the 3' oxygen of the deoxyribose.

20. The method of claim 18, further comprising using a deblocking agent to remove the 3' blocking group of the incorporated nucleotides.

21. The method of claim 20, further comprising washing the solid support before the next incorporation cycle.

22. The method of claim 21, wherein the steps are repeated a number of cycles to determine the sequence of the target nucleic acids.

23. The method of claim 18, wherein at least one type of nucleotide comprises the following structure:

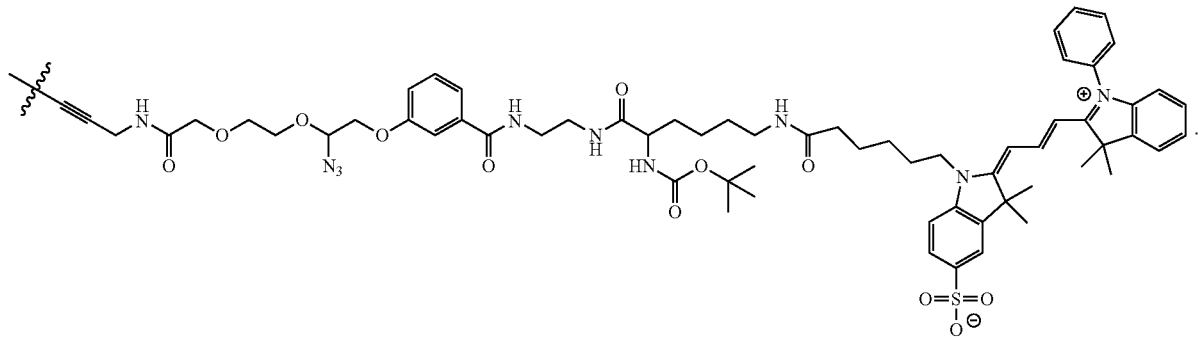 [SMILES: *C#CCNC(=O)COCCOC(COc1cccc(C(=O)NCCNC(=O)C(CCCCNC(=O)CCCCCN2/C(=C/C=C/C3=[N+](c4ccccc4)c4ccccc4C3(C)C)C(C)(C)c3cc(S(=O)(=O)[O-])ccc32)NC(=O)OC(C)(C)C)c1)N=[N+]=[N-]]
24. The method of claim 23, wherein the nucleotide comprises a 3' azidomethyl blocking group attached to the 3' oxygen of the deoxyribose.
25. The method of claim 24, wherein the nucleotide has an A base.
26. The method of claim 24, wherein the nucleotide has a T base.
27. The method of claim 24, wherein the nucleotide has a C base.
* * * * *